United States Patent
Bayly et al.

(10) Patent No.: US 6,465,444 B2
(45) Date of Patent: Oct. 15, 2002

(54) ARYLDIFLUOROMETHYLPHOSPHONIC ACIDS WITH SULFUR-CONTAINING SUBSTITUENTS AS PTP-1B INHIBITORS

(75) Inventors: Christopher Bayly, Beaconsfield (CA); Mitsuru Ohkubo, Ushiku (JP)

(73) Assignees: Merck Frosst Canada & Co., Kirkland; Banyu Pharmaceutical Co., Ltd., Tokyo ( * ) Notice: Subject to any disclaimer, the term of this patent is extended or adjusted under 35 U.S.C. 154(b) by 0 days.

(21) Appl. No.: 09/813,499

(22) Filed: Mar. 21, 2001

(65) Prior Publication Data

US 2002/0002149 A1 Jan. 3, 2002

Related U.S. Application Data

(60) Provisional application No. 60/191,369, filed on Mar. 22, 2000.

(51) Int. Cl.$^7$ .............................................. A61K 31/663
(52) U.S. Cl. ........................ 514/127; 514/80; 514/82; 562/20; 564/22; 564/23
(58) Field of Search .............................. 562/20, 11, 12, 562/24, 8, 23; 514/75, 79, 80, 82, 102, 107, 114, 126, 127; 564/22, 23

(56) References Cited

U.S. PATENT DOCUMENTS 6,066,715 A    5/2000  Desmarais et al.
6,174,874 B1 * 1/2001  Wang et al. .................... 514/80

FOREIGN PATENT DOCUMENTS

| WO | WO 97/40017 | 10/1997 |
| WO | WO 98/20156 | 5/1998 |
| WO | WO 99/31066 | 6/1999 |
| WO | WO 99/47529 | 9/1999 |
| WO | WO 00/17211 | 3/2000 |
| WO | WO 00/69889 | 11/2000 |
| WO | WO 01/46203 | 6/2001 |
| WO | WO 01/46204 | 6/2001 |
| WO | WO 01/46205 | 6/2001 |
| WO | WO 01/46206 | 6/2001 |

OTHER PUBLICATIONS

CA:133:332980 Biochem Pharmacol abs Kennedy et al 60(7) pp. 877–883 2000.*
Biochemistry by Tang et al. 38 pp. 3793–3803 1999.*
CA:130:267518 by Yokomatsu et al 9(4) pp. 529–532 1999.*
Pierre L. Beaulieu, et al., J. Med. Chem. 1999, 42, 1757–1766.
K. Blades, et al., Chem. Commun., 1615–1616, 1996.
Terrence R. Burke, Jr., et al., Bioorganic & Medicinal Chemistry Letters 9 (1999) 347–352.
Neil A. Caplan, et al., Bioorganic & Medicinal Chemistry Letters 8 (1998) 515–520.
Paul S. Charifson, et al., Biochemistry 1997, 36, 6283–6293.
G. Stuart Cockerill, et al., Tetrahedron Letters 40 (1999) 2601–2604.
G. Stuart Cockerill, et al., J. Chem. Soc., Perkin Trans. 1, 2000, 2591–2599.
Sylvie Desmarais, et al., Biochem. J. (1999) 337, 219–223.
Mikhail F. Gordeev, et al., Tetrahedron Letters, vol. 35, No. 41, pp. 7585–7588, 1994.
Hong, J. Enzyme Inhib., vol. 12, pp. 191–203, 1997.
Christopher c. Kotoris, Bioorganic & Medicinal Chemistry Letters 8 (1998) 3275–3280.
Christopher C. Kotoris, J. Org. Chem. 1998, 63, 8052–8057.
Meng Taing, et al., Biochemistry 1999, 38 3793–3803.
Scott D. Taylor, et al., Bioorganic & Medicinal Chemistry 6 (1998) 1457–1468.
Scott D. Taylor, et al., Bioorganic & Medicinal Chemistry 6 (1998) 2235.
Scott D. Taylor, et al., Tetrahedron Letters, vol. 37, No. 45, pp. 8089–8092, 1996.
Scott D. Taylor, et al., Tetrahedron 54 (1998) 1691–1714.
Quigping Wang, et al., Bioorganic & Medicinal Chemistry Letters 8 (1998) 345–350.
Zhu–Jun Yao, et al., Tetrahedron 55 (1999) 2865–2874.
Bin Ye, et al., Tetrahedron, vol. 52. No. 30., pp. 9963–9970, 1996.
Tsutomu Yokomatsu, et al., Tetrahedron 54 (1998) 9341–9356.
Tsutomu Yokomatsu, et al., Bioorganic & Medicinal Chemistry Letters 9 (1999) 529–532.

* cited by examiner

Primary Examiner—Jean F. Vollano
(74) Attorney, Agent, or Firm—James L. McGinnis; Melvin Winokur

(57) ABSTRACT

The invention encompasses the novel class of compounds represented by the formula below, which are inhibitors of the PTP-1B enzyme.

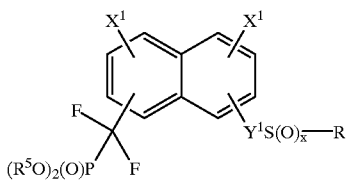

The invention also encompasses pharmaceutical compositions and methods of treating or preventing PTP-1B mediated diseases, including diabetes.

31 Claims, No Drawings

ARYLDIFLUOROMETHYLPHOSPHONIC ACIDS WITH SULFUR-CONTAINING SUBSTITUENTS AS PTP-1B INHIBITORS

CROSS REFERENCE TO RELATED APPLICATIONS

U.S. application Ser. No. 09/398,356, filed on Sep. 17, 1999, now U.S. Pat. No. 6,174,874, issued Jan. 16, 2001; U.S. application Ser. No. 09/570,092, filed May 12, 2000, now U.S. Pat. No. 6,365,592; U.S. application Ser. Nos. 09/745,199, 09/745,211, 09/745,220 and 09/745,222, all filed on Dec. 21, 2000; and U.S. application Ser. No. 09/813,489, filed on even date herewith, all contain related subject matter. This application claims priority from U.S. Provisional Application No. 60/191,369, filed on Mar. 22, 2000.

BACKGROUND OF THE INVENTION

This invention relates to a novel class of phosphonic acid derivatives that are inhibitors of PTP-1B.

Protein tyrosine phosphatases are a large family of transmembrane or intracellular enzymes that dephosphorylate substrates involved in a variety of regulatory processes (Fischer et al., 1991, Science 253:401–406). Protein tyrosine phosphatase-1B (PTP-1B) is a ~50 kd intracellular protein present in abundant amounts in various human tissues (Charbonneau et al., 1989, Proc. Natl. Acad. Sci. USA 86:5252–5256; Goldstein, 1993, Receptor 3:1–15).

Determining which proteins are substrates of PTP-1B has been of considerable interest. One substrate which has aroused especial interest is the insulin receptor. The binding of insulin to its receptor results in autophosphorylation of the receptor, most notably on tyrosines 1146, 1150, and 1151 in the kinase catalytic domain (White & Kahn, 1994, J. Biol. Chem. 269:1–4). This causes activation of the insulin receptor tyrosine kinase, which phosphorylates the various insulin receptor substrate (IRS) proteins that propagate the insulin signaling event further downstream to mediate insulin's various biological effects.

Seely et al., 1996, Diabetes 45:1379–1385 ("Seely") studied the relationship of PTP-1B and the insulin receptor in vitro. Seely constructed a glutathione S-transferase (GST) fusion protein of PTP-1B that had a point mutation in the PTP-1B catalytic domain. Although catalytically inactive, this fusion protein was able to bind to the insulin receptor, as demonstrated by its ability to precipitate the insulin receptor from purified receptor preparations and from whole cell lysates derived from cells expressing the insulin receptor.

Ahmad et al., 1995, J. Biol. Chem. 270:20503–20508 used osmotic loading to introduce PTP-1B neutralizing antibodies into rat KRC-7 hepatoma cells. The presence of the antibody in the cells resulted in an increase of 42% and 38%, respectively, in insulin stimulated DNA synthesis and phosphatidyinositol 3' kinase activity. Insulin receptor autophosphorylation and insulin receptor substrate-1tyrosine phosphorylation were increased 2.2 and 2.0-fold, respectively, in the antibody-loaded cells. The antibody-loaded cells also showed a 57% increase in insulin stimulated insulin receptor kinase activity toward exogenous peptide substrates.

Recently, Kennedy et al., 1999, Science 283:1544–1548 showed that protein tyrosine phosphatase PTP-1B is a negative regulator of the insulin signalling pathway, suggesting that inhibitors of this enzyme may be beneficial in the treatment of Type 2 diabetes. Mice lacking PTP-1B are resistant to both diabetes and obesity.

Thus, inhibitors of PTP-1B may improve insulin-sensitivity. They may have utility in controlling or treating Type 1 and Type 2 diabetes, in improving glucose tolerance, and in improving insulin sensitivity in patients in need thereof. The compounds may also be useful in treating or preventing cancer, neurodegenerative diseases and the like. PTP-1B inhibitors are not currently used in any medications, and new compounds are needed to find compounds that are suitable for medicinal uses

SUMMARY OF THE INVENTION

Compounds represented by formula 1, including pharmaceutically acceptable salts thereof, and prodrugs thereof, are PTP-1B inhibitors that may be useful in the treatment of diabetes and related medical conditions, and may also be useful in the treatment of other PTP-1B mediated diseases or conditions.

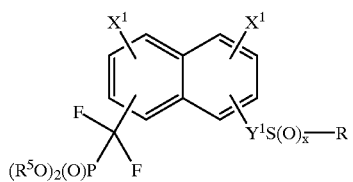

I

In the compounds of formula I:

Each $X^1$ is independently selected from the group consisting of: H, OH, halogen, CN, $CO_2H$, $CO_2C_{1-6}$alkyl, $CO_2C_{2-6}$alkenyl, $OC_{1-6}$alkyl, $OC_{2-6}$alkenyl, $C(O)C_{1-6}$alkyl, $C(O)C_{2-6}$alkenyl, $OC(O)C_{1-6}$alkyl, $OC(O)C_{2-6}$alkenyl, $S(O)_x C_{1-6}$alkyl, $S(O)_xC_{2-6}$alkenyl, $C_{1-6}$ alkyl, $C_{2-6}$alkenyl, $S(O)_2 NR^1R^2$, $C(O)NR^1R^2$, and $NR^1R^2$, wherein each alkyl group and each alkenyl group in each substituent is optionally substituted with one or more groups independently selected from (a) 1–13 halogen atoms and/or (b) 1–2 substituents independently selected from $OC_{1-3}$ alkyl, $C(O)C_{1-3}$ alkyl, $OC(O)C1-3$alkyl, $CO_2H$, and $CO_2C_{1-3}$alkyl;

$X^1$, $CF_2P(O)(OR^5)_2$ and $Y^1S(O)_xR$ are substituted onto any position of either ring;

Each x is independently 0, 1, or 2;

$R^5$ is H;

$R^1$ and $R^2$ are each independently selected from the group consisting of H and $C_{1-4}$alkyl, wherein said alkyl substituents are optionally substituted with 1–9 halogen atoms;

Each halogen is independently selected from I, Cl, Br and F;

$Y^1$ is selected from the group consisting of a bond, a $C_{1-4}$ alkylene group, and a $C_{2-4}$ alkenylene group, wherein the alkylene group and the alkenylene group are optionally substituted with one or more of the following groups: (a) 1–8 halogen atoms, and/or (b) 1–2 substituents independently selected from OH and $OC_{1-4}$ alkyl, where $OC_{1-4}$ alkyl is optionally substituted with 1–9 halogen atoms;

R is selected from the group consisting of $C_{1-10}$ alkyl, $C_{2-10}$alkenyl, $C_{2-10}$alkadienyl, $C_{2-10}$alkynyl, $Ar^1$, and $Het^1$, wherein said alkyl, alkenyl, alkadienyl, and alkynyl are optionally substituted with one substituent selected from $Ar^1$ and $Het^1$, and are optionally also substituted with one or more groups independently selected from (a) 1–21 halogen atoms, and (b) 1–2 substituents independently selected from OH, CN, $CO_2H$, $CO_2C_{1-6}$ alkyl, $CO_2C_{2-6}$ alkenyl, $OC_{1-6}$alkyl, $OC_{2-6}$ alkenyl, $OC(O)C_{1-6}$alkyl, $OC(O)C_{2-6}$alkenyl, $C(O)C_{1-6}$alkyl, $C(O)C_{2-6}$alkenyl, C(O)Aryl, OC(O) Aryl, OAryl, $CO_2$Aryl, $S(O)_xC_{1-6}$alkyl, $S(O)_xC_{2-6}$alkenyl, $S(O)_2NR^1R^2$, $C(O)NR^1R^2$, and $NR^1R^2$, wherein said alkyl groups and said alkenyl groups of said substituents are optionally substituted with 1–13 halogen atoms;

$Het^1$ is a 5–10 membered aromatic ring system comprising 1 ring or 2 rings fused together and 1–4 heteroatoms selected from O, N, S(O)x, and combinations thereof, and 0–2 carbonyl groups, wherein one of the fused rings is optionally a benzene ring, and Het1 is optionally substituted with one or more groups independently selected from (a) one group selected from $CF_2P(O)(OR^5)_2$, $CO_2H$, $CF_2CO_2H$, $P(O)(OR^5)_2$, and $SO_2R^4$, and/or (b) 1–2 groups independently selected from $R^3$;

$Ar^1$ is phenyl or naphthyl, optionally substituted with one or more groups independently selected from (a) one group selected from $CF_2P(O)(OR^5)_2$, $CO_2H$, $CF_2CO_2H$, $P(O)(OR^5)_2$, $SO_2R^4$, and $Ar^2$, and/or (b) 1–2 groups selected from $R^3$;

$Ar^2$ is phenyl, naphthyl or a 5–10 membered aromatic ring system comprising 1 ring or 2 rings fused together and 1–4 heteroatoms selected from O, N, $S(O)_x$, and combinations thereof, and 0–2 carbonyl groups, wherein one of said fused rings is optionally a benzene ring, wherein $Ar^2$ is optionally substituted with one or more of the following groups: (a) one group selected from $CF_2P(O)(OR^5)_2$, $CO_2H$, $CF_2CO_2H$, $P(O)(OR^5)_2$, and $SO_2R^4$, and/or (b) 1–2 groups selected from $R^3$;

$R^3$ is selected from the group consisting of halogen, OH, CN, $CO_2H$, $CO_2C_{1-10}$ alkyl, $CO_2C_{2-10}$ alkenyl, $OC_{1-10}$ alkyl, $OC_{2-10}$ alkenyl, $C_{1-10}$alkyl, $C_{2-10}$alkenyl, $OC(O)C_{1-10}$alkyl, $OC(O)C_{2-10}$alkenyl, $C(O)C_{1-10}$alkyl, $C(O)C_{2-10}$alkenyl, C(O)Aryl, OC(O)Aryl, OAryl, $CO_2$Aryl, $S(O)_xC_{1-10}$alkyl, $S(O)_xC_{2-10}$alkenyl, $S(O)_2NR^1R^2$, $C(O)NR^1R^2$, $NR^1R^2$, Aryl, and Het, wherein each alkyl group and each alkenyl group of each substituent is optionally substituted with one or more groups independently selected from (a) 1–21 halogen atoms and/or (b) 1–2 substituents independently selected from OH, $OC_{1-3}$ alkyl, $CO_2H$, $CO_2C_{1-3}$alkyl, $C(O)C_{1-3}$alkyl, $OC(O)C_{1-3}$alkyl, and phenyl, wherein phenyl is optionally substituted with 1–3 substituents independently selected from $OCH_3$, $OCF_3$, Cl and F, and the $C_{1-3}$ alkyl groups of the substituents are optionally substituted with one or more groups independently selected from (a) 1–7 halogen atoms and/or (b) 1–2 phenyls, wherein said phenyls are optionally substituted with 1–3 halogen atoms;

Aryl is a 6–14 membered aromatic carbocyclic moiety comprising 1 ring or 2–3 fused rings, wherein said Aryl is optionally substituted with 1–3 substituents independently selected from $C_{1-3}$alkyl, halogen, $OC_{1-3}$ alkyl, $C(O)C_{1-3}$alkyl, $OC(O)C_{1-3}$alkyl, $CO_2H$, and $CO_2C_{1-3}$ alkyl, wherein said alkyl groups in said substituents are optionally substituted with 1–7 halogen atoms;

Het is a 5–10 membered aromatic ring system comprising 1–4 heteroatoms selected from N, S(O)x, O, and mixtures thereof, and 0–2 carbonyl groups, wherein said Het comprises 1 ring or 2 fused rings, one of which fused rings may be a benzene ring, and said Het is optionally substituted with 1–3 substituents independently selected from $C_{1-3}$alkyl, halogen, OC1–3 alkyl, $C(O)C_{1-3}$alkyl, $OC(O)C_{1-3}$alkyl, $CO_2H$, and $C_2C_{1-3}$ alkyl, wherein said alkyl groups are optionally substituted with 1–7 halogen atoms;

Alkyl, alkenyl, alkadienyl and alkynyl are linear, branched or cyclic hydrocarbon structures, or combinations thereof containing the indicated number of carbon atoms and substituted as indicated, wherein said alkyl, alkenyl, alkadienyl and alkynyl respectively are saturated, comprise one double bond, comprise 2 double bonds, or comprise one triple bond; and $R^4$ is phenyl or $C_{1-4}$ alkyl, wherein said phenyl is optionally substituted with one or more groups independently selected from (a) 1–3 halogen atoms and (b) 1–2 $C_{1-3}$ alkyl or $C_{1-3}$alkoxy groups, which are optionally substituted with 1–7 halogen atoms, and said $C_{1-4}$ alkyl is optionally substituted with one or more groups independently selected from: (a) 1–9 halogen atoms and/or (b) 1–2 $C_{1-3}$ alkoxy groups, which are optionally substituted with 1–7 halogen atoms.

Methods of treating and controlling diabetes, obesity, and other diseases and conditions using the compounds of Formula I are taught herein. Pharmaceutical compositions and combination treatments are also disclosed herein.

DETAILED DESCRIPTION OF THE INVENTION

The compounds of Formula I have numerous embodiments, as summarized below.

In one embodiment of the compounds of Formula I, the halogen atom substituents are independently selected from Cl, Br, and F.

In another embodiment, $X^1$ is H, and the second group $X^1$ is selected from the group consisting of a halogen atom, $CH_3$, $OCH_3$, OH and $CO_2H$.

Another embodiment comprises compounds of Formula I, wherein one group $X^1$ is H; the second group $X^1$ is Cl, F, or Br; and the $Y^1$ substituent and the group $CF_2 P(O)(OR^5)_2$ are on different rings of Formula I. One preferred subset of compounds is comprised of compounds in which one group $X^1$ is Br and is on a carbon adjacent to the carbon to which $CF_2P(O)(OR^5)_2$ is attached. Another group of compounds is comprised of compounds in which $Y^1S(O)_xR$ and $CF_2P(O)(OR^5)_2$ are attached to the 2,7-positions of the naphthalene ring.

Another preferred group of compounds includes compounds in which $Y^1$ is a bond, $CH_2$, or linear $C_{2-4}$alkyl. A subgroup of these compounds is made up of compounds in which $Y^1$ is a bond, $CH_2$, or $C_2H_4$.

Another preferred group of compounds comprises those compounds in which the group Y1 of Formula I is alkylene or alkenylene, where each carbon atom that makes up Y1 is linear or monobranched. Similarly, all the carbon atoms that make up the main carbon chain in the group R are linear or monobranched, where R can be alkyl, alkenyl, alkadienyl or alkynyl. The carbon atoms are defined as linear when there are no hydrocarbon branches on any carbon atom, and are defined as monobranched when there is one hydrocarbon branch on the carbon. Dibranched carbons are fully branched, having two hydrocarbon substituents (i.e. they are quaternary carbon atoms). In other embodiments, only the first two carbons of Y1 and R on each side of S are linear or monobranched.

In a preferred embodiment of the compounds having Formula I, $Y^1$ is selected from the group consisting of a linear $C_{1-4}$ alkylene group and a linear $C_{1-4}$ alkenylene group and is optionally substituted with one or more groups independently selected from (a) 1–8 halogen atoms, and/or (b) 1–2 substituents independently selected from OH and $OC_{1-4}$ alkyl, said $OC_{1-4}$ alkyl being optionally substituted with 1–9 halogen atoms; and R is selected from the group consisting of a linear $C_{1-10}$ alkyl, linear $C_{2-10}$alkenyl, linear $C_{2-10}$alkadienyl, and linear $C_{2-10}$alkynyl, wherein R is substituted with $Ar^1$ or $Het^1$, and R is optionally also substituted with one or more groups independently selected from (a) 1–21 halogen atoms, and/or (b) 1–2 substituents independently selected from OH, CN, $CO_2H$, $CO_2C_{1-6}$ alkyl, $CO_2C_{2-6}$ alkenyl, $OC_{1-6}$alkyl, $OC_{2-6}$ alkenyl, $OC(O)C_{1-6}$alkyl, $OC(O)C_{2-6}$alkenyl, $C(O)C_{1-6}$ alkyl, $C(O)C_{2-6}$alkenyl, $C(O)Aryl$, $OC(O)Aryl$, $OAryl$, $CO_2Aryl$, $S(O)_xC_{1-6}$alkyl, $S(O)_xC_{2-6}$alkenyl, $S(O)_2NR^1R^2$, $C(O)NR^1R^2$, and $NR^1R^2$, wherein the alkyl groups and the alkenyl groups of the substituents are optionally substituted with 1–13 halogen atoms.

In another preferred embodiment of the compounds having formula I, R is selected from the group consisting of $C_{1-4}$ alkyl and $C_{1-4}$ alkenyl and has an $Ar^1$ substituent. $Ar^1$ is phenyl or naphthyl, and is optionally substituted with one group $CF_2P(O)(OR^5)_2$, and is optionally also substituted with 1–2 $R^3$ groups, where $R^3$ is selected from the group consisting of Br, Cl, F, OH, and $C_{1-3}$ alkyl. $Ar^1$ thus can be substituted only with $CF2P(O)(OR^5)_2$, or it can be substituted only with 1–2 $R^3$ groups, or it can be substituted with both $CF_2P(O)(OR^5)_2$ and 1 or 2 $R^3$ groups. Alternatively, $Ar^1$ can be unsubstituted. In a particularly preferred group of compounds, $R^3$ is Br.

Another embodiment comprises compound having formula I, where:

R is $C_{1-4}$ alkyl or $C_{1-4}$ alkenyl, and is substituted with $Ar^1$;

$Ar^1$ is phenyl or naphthyl and is substituted with $Ar^2$;

$Ar^2$ is a 5–10 membered aromatic ring system having 1 ring or 2 rings fused together and 1–4 heteroatoms selected from 0, N, $S(O)_x$, and combinations thereof, and 0–2 carbonyl groups, wherein one of the fused rings is optionally a benzene ring, and $Ar^2$ is optionally substituted with: (a) $P(O)(OH)_2$ or $CO_2H$; and/or (b) 1–2 groups $R^3$;

$R^3$ is selected from $C_{1-10}$ alkyl, $OC_{1-10}$alkyl, $C(O)Aryl$, and Aryl, where said $C_{1-10}$alkyl and $OC_{1-10}$ alkyl are optionally substituted with 1–2 substituents independently selected from $OC_{1-3}$ alkyl, phenyl, and $CO_2H$; and $X^1$, $X^2$, $R^1$, $R^2$, $R^4$, $R^5$, x, $Y^1$, Aryl, Het, and $Het^1$ are as defined previously.

In the embodiment described immediately above, preferred substituents $Ar^2$ include quinoline, thiazole, tetrazole, pyridine, pyrazole, oxadiazole, isothiazole, and oxazole.

A group of compounds that are related to the embodiment described above includes compounds in which:

R is $C_{1-4}$ alkyl and $C_{1-4}$ alkenyl and is substituted with $Ar^1$;

$Ar^1$ is phenyl and is substituted with $Ar^2$;

$Ar^2$ is phenyl, and is optionally unsubstituted or is optionally substituted with one or more substituents selected from (a), (b) or both (a) and (b), such that (a) one substituent is optionally chosen from $P(O)(OR^5)_2$, $CO_2H$, and $SO_2R^4$, and (b) 1–2 substituents are optionally chosen from $R^3$;

$R^4$ is phenyl or $C_{1-4}$ alkyl;

$R^3$ is selected from OH, Br, $OC_{1-10}$alkyl, $C_{1-10}$alkyl, Aryl, and $C_{1-10}$alkenyl, and each alkyl group and each alkenyl group is optionally substituted with $OC_{1-3}$ alkyl or phenyl; and $X^1$, $X^2$, $R^1$, $R^2$, $R^5$, x, $Y^1$, Aryl, Het and $Het^1$ are as previously defined.

The invention also comprises prodrugs of the compounds of Formula I. In these, one or more of $R^5$ is a moiety that is converted to H under physiological conditions during or after administration to a mammalian patient, and the remainder of $R^5$ moieties are H or pharmaceutically acceptable salts therof. Conversion of the prodrug, as by hydrolysis or metabolism, yields a compound having Formula I, where $R^5$ is H, or a pharmaceutically acceptable salt thereof. Prodrugs are described in more detail below.

A specific compound having formula I is described, and schemes for synthesizing the compound are also provided.

Methods of treating, preventing, or controlling diabetes and other diseases using the compounds of Formula I are disclosed herein. A method of treating, controlling or preventing diabetes and complications thereof in a mammalian patient in need of such treatment includes administering to the patient an anti-diabetic effective amount of a compound of Formula I. A method of treating, controlling or preventing obesity in a mammalian patient in need of such treatment comprises the administration to the patient an anti-obesity effective amount of a compound in accordance with claim 1. Such methods also include the administration of a second compound, which may be an anti-diabetic compound, an anti-obesity compound, or an HMG-CoA reductase inhibitor, in an amount effective to treat, control or prevent diabetes or obesity, or to improve a poor lipid profile.

A method of treating, controlling or preventing atherosclerosis in a mammalian patient in need of such treatment comprises administering to the patient an effective amount of a compound of Formula I and an effective amount of an HMG-CoA reductase inhibitor.

More generally, compounds of Formula I may be used as the active compound in a method for treating, preventing, or controlling one or more diseases or conditions selected from Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease. The method comprises the administration of an effective amount of the compound of Formula I. Combination treatments can also be used in which case, the method comprises the administration of a compound of Formula I and an effective amount of one or more pharmaceutically active compounds selected from the group consisting of an HMG-CoA reductase inhibitor, an anti-obesity agent, and an antidiabetic compound.

Pharmaceutical compositions also can be made using the compounds of Formula I. Compositions that are suitable for the treatment, prevention or control of one or more diseases or conditions selected from Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease contain an effective amount of a compound of Formula I in combination with a pharmaceutically acceptable carrier.

Such pharmaceutical compositions may also include a second anti-diabetic agent or an anti-obesity agent. They may also include a cholesterol lowering agent. Pharmaceutical compositions may therefore include: (1) an effective amount of a compound of Formula I, (2) an effective amount of one or more pharmaceutically active compounds selected from the group consisting of an IBMG-CoA reductase inhibitor, an anti-obesity agent, and an anti-diabetic agent, and (3) a pharmaceutically acceptable carrier.

Such pharmaceutical compositions that contain a second active compound or composition and that are suitable for the treatment, prevention or control of one or more diseases or conditions selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, may be comprised of the following:

(1) an effective amount of a compound of Formula 1;
(2) an effective amount of one or more pharmaceutically active compounds listed below; and
(3) a pharmaceutically acceptable carrier; where the pharmaceutically active compounds are selected from the group consisting of:
 (a) insulin sensitizers including (i) PPARγ agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin;
 (b) insulin or insulin mimetics;
 (c) sulfonylureas such as tolbutamide and glipizide, or related materials;
 (d) α-glucosidase inhibitors (such as acarbose);
 (e) cholesterol lowering agents such as (i) HMG-CoA reductase inhibitors (lovastatin, simvastatin and pravastatin, fluvastatin, atorvastatin, rivastatin and other statins), (ii) sequestrants (cholestyramine, colestipol and a dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and benzafibrate), (v) inhibitors of cholesterol absorption for example beta-sitosterol and (acyl CoA:cholesterol acyltransferase) inhibitors for example melinamide and (vi) probucol;
 (f) PPARα/γ agonists;
 (g) antiobesity compounds such as appetite suppressants, fenfluramine, dexfenfluramine, phentiramine, sulbitramine, orlistat, neuropeptide Y5 inhibitors (NP Y5 receptor antagonosts), leptin, which is a peptidic hormone, β$_3$ adrenergic receptor agonists, and PPARy antagonists and partial agonists;
 (h) ileal bile acid transporter inhibitors; and
 (i) insulin receptor activators.

The second pharmaceutically active compounds that are used in the combination pharmaceutical compositions described above may be summarized as:
 (a) insulin sensitizers, PPAR-gamma agonists, partial agonists, and antagonists, PPAR-alpha agonists, PPAR-delta agonsts, and biguanides;
 (b) insulin and insulin mimetics;
 (c) sulfonylureas;
 (d) α-glucosidase inhibitors;
 (e) cholesterol lowering agents selected from the group consisting of (i) HMG-CoA reductase inhibitors; (ii) sequestrants, (iii) nicotinyl alcohol, nicotinic acid and salts thereof, (iv) PPARα agonists, (v) inhibitors of cholesterol absorption; and (vi) probucol;
 (f) PPARα/γ agonists;
 (g) antiobesity compounds selected from the group consisting of appetite suppressants, fenfluramine, dexfenfluramine, phentiramine, sulbitramine, orlistat, neuropeptide Y5 inhibitors (NP Y5 receptor antagonosts), leptin, β3 adrenergic receptor agonists, and PPARγ antagonists and partial agonists;
 (h) ileal bile acid transporter inhibitors; and
 (i) insulin receptor activators.

Abbreviations

The following abbreviations have the indicated meanings:

AA=arachidonic acid
Ac=acetyl
AIBN=2.2'-azobisisobutyronitrile
Bn=benzyl
BSA=bovine serum albumin
Bz=benzoyl
CHO=chinese hamster ovary
CMC=1-cyclohexyl-3-(2-morpholinoethyl) carbodiimidemetho-p-toluenesulfonate
DAST=diethylamino sulfur trifluoride
DBU=diazabicyclo[5.4.0]undec-7-ene
DMAP=4-(dimethylamino)pyridine
DMF =N,N-dimethylformamide
DMSO=dimethyl sulfoxide
Et$_3$N=triethylamine
HATU=O-(7-azabenzotriazol-1-yl)-1,1,3,3-tetramethyluronium hexafluorophosphate
HBSS=Hanks balanced salt solution
HEPES=N $^1$-[2-Hydroxyethyl]piperazine-N$^4$-[2-ethanesulfonic acid]
HWB=human whole blood
KHMDS=potassium hexamethyldisilazane
LDA=lithium diisopropylamide
LPS=lipopolysaccharide
mCPBA=metachloro perbenzoic acid
MMPP=magnesium monoperoxyphthalate
Ms=methanesulfonyl=mesyl
MsO=methanesulfonate=mesylate
NBS=N-bromosuccinimide
NCS=N-chlorosuccinimide
NIS=N-iodosuccinimide
NSAID=non-steroidal anti-inflammatory drug
Oxone®=potassium peroxymonosulfate
PCC=pyridinium chlorochromate
PDC=pyridinium dichromate
PPA=polyphosphoric acid
PTP=protein tyrosine phosphatase
r.t.=room temperature
rac.=racemic
Tf=trifluoromethanesulfonyl=triflyl
TFA=trifluoroacetic acid
TFAA=trifluoroacetic anhydride
TfO=trifluoromethanesulfonate=triflate
TEF=tetrahydrofuran
TLC=thin layer chromatography
Ts=p-toluenesulfonyl=tosyl
TsO=p-toluenesulfonate=tosylate
Tz=1H (or 2H)-tetrazol-5-yl Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl Dose Abbreviations
bid=bis in die=twice daily
qid=quater in die=four times a day
tid=ter in die=three times a day Alkyl means linear, branched and cyclic structures, and combinations thereof, containing the indicated number of carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, cyclopropyl, cyclopentyl, cycloheptyl, cyclopropylmethyl, methylcyclopropy, adamantyl, cyclododecylmethyl, 2-ethyl-1-bicyclo[4.4.0]decyl and the like.

Fluoroalkyl means alkyl groups of the indicated number of carbon atoms in which one or more hydrogens is replaced by fluorine. Examples are —CF$_3$, —CH$_2$CH$_2$F, —CH$_2$CF$_3$, c-Pr—F$_5$, c-Hex—F$_{11}$ and the like. Haloalkyl has the analogous meaning for replacement of one or more hydrogen atoms with any halogen (Cl, Br, F, and/or I).

Alkenyl means linear, branched and cyclic structures, and combinations thereof containing a double bond with the indicated number of carbon atoms. Examples of alkenyl groups include allyl, 2-butenyl, 3-butenyl, 2-pentenyl, 2-cyclopentenyl, 3-cyclopentenyl, 2-methyl-cyclohexenyl, 2-cyclohexenyl, 3-cyclohexenyl and the like. Alkadienyl means the diunsaturated counterpart to alkenyl.

Alkynyl means linear, branched and cyclic structures, and combinations thereof containing a triple bond with the indicated number of carbon atoms. Examples of alkynyl groups include propargyl, 2-butynyl, 3-butynyl, 2-pentynyl, cyclopropylethynyl, and the like.

Alkylene, alkenylene, alkynylene, fluoroalkylene, alkadienylene, and the like, where the suffix "ene" has been added to the name of the monovalent radicals alkyl, alkenyl, alkynyl, fluoroalkyl, alkadienyl, and the like, describe divalent radicals that are the same as their monovalent counterparts, except that two hydrogen atoms rather than one are absent so that the radical will have two points of attachment, in addition to attachments to substituents which may also be present.

Aryl groups include 6–14 membered carbocyclic aromatic ring systems comprising 1–3 phenyl rings. If two or more aromatic rings are present, then the rings are fused together, so that adjacent rings share a common side. Examples are benzene, naphthalene, anthracene and phenanthrene. Preferred aryl groups are benzene and naphthalene. Substitutions on these are defined herein.

Heteroaryl as used herein represents a 5–10 membered aromatic ring system comprising one ring or two fused rings, 1–4 heteroatoms selected from the groups consisting of N, O, S(O)x, and mixtures thereof wherein x is 0, 1 or 2, and 0–2 carbonyl groups. Carbonyl groups, when present, are not counted as heteroatoms. Heteroaryl includes, but is not limited to, furanyl, diazinyl, imidazolyl, isoxazolyl, isothiazolyl, oxadiazolyl, oxazolyl, pyrazolyl, pyridyl, pyrrolyl, tetrazinyl, thiazolyl, thienyl, triazinyl, triazolyl, 1H-pyrrole-2,5-dionyl, 2-pyrone, 4-pyrone, pyrrolopyridine, furopyridine and thienopyridine. Heteroaryl also includes benzoheteroaryl, defined below. Preferred heteroaryl substituents include quinoline, thiazole, tetrazole, pyridine, imidazole, isoxazole, isothiazole, oxazole, pyrazole, thiophene, oxadiazole, benzothiophene, benzothiazole, benzotriazole, benzothiadiazole, and isoquinoline.

Benzoheteroaryl is a subset of heteroaryl and includes aromatic ring systems containing one or more heteroatoms which also have a fused 6-membered benzene ring, such as 2H-1-benzopyran-2-one, 4H-1-benzopyran-4-one, 2(3H) benzofuranone, 3(2H)benzofuranone, 2,3-dihydrobenzofuran, 2,3-dihydrobenzothiophene, indole, benzofuran, benzothiophene, benzimidazole, benzoxazole, benzothiazole, benzotriazole, benzothiadiazole, 1H-isoindole-1,3(2H)-dione, quinoline, and isoquinoline.

Another subset of heteroaryls includes 5-membered heteroaryls, such as the following:

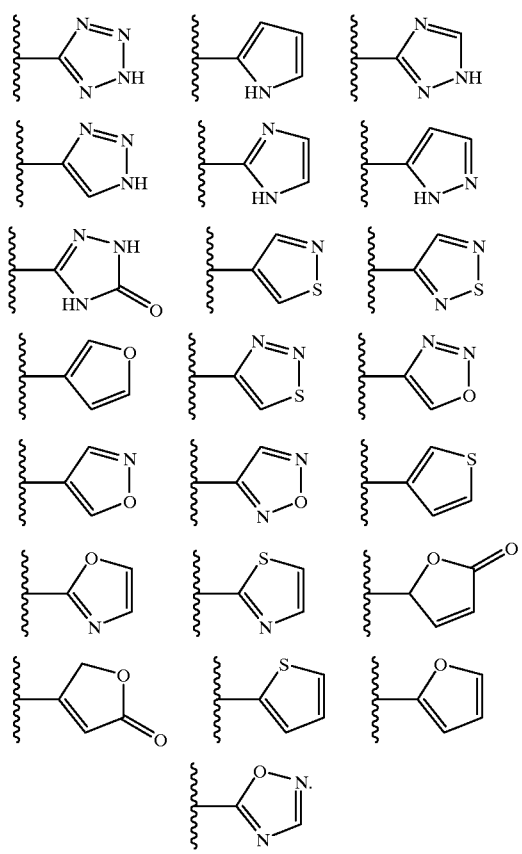

When a heteroaromatic ring is specified as optionally having one or more heteroatoms, this means that at least one heteroatom is present, selected from O, S, SO, SO$_2$ and N, and up to 4 such heteroatoms may be present, depending upon the size of the ring specified. When SO or S(O)$_2$ is in a heteroaromatic ring, only the S is part of the actual ring structure, whereas the O atoms are attached to the S but are exocyclic to the actual ring structure.

When a moiety is specified as being optionally substituted with one or more than one substituent, then the same moiety may also optionally not have the substituent(s) (and remain unsubstituted), unless otherwise stated.

Finally, when a list of possible choices is provided for a given substituent, and the substituent is used in more than one position in a chemical formula, the selection of a choice for the substituent in each position is independent of other selections, unless the definition specifically says otherwise.

Metabolites-Prodrugs

Metabolites of the compounds of this invention that are therapeutically active and that are described by formula I also are within the scope of the claimed invention, as are prodrugs, which are compounds that are converted to the claimed active compounds or salts of the claimed active compounds after they have been administered to a patient. A non-limiting example of a prodrug of the phosphonic acids of this invention would be a monoester or diester of one or more phosphonic acid groups, where the ester functionality preferably has a structure that makes it easily hydrolyzed or metabolized after administration to a patient. Examples of prodrugs include $C_{1-6}$ alkyl esters of the phosphonic acids. Prodrugs that have structures that are more easily hydrolyzed or metabolized are generally more preferred. Examples are illustrated by the structures below, where R'=H or a $C_{1-6}$ alkyl group, and R"=$C_{1-6}$ alkyl group or —$OC_{1-6}$ alkyl group, and Q is the residue of the molecule that is attached to the —$CF_2PO_3H_2$ or —$PO_3H_2$ group in formula I. The alkyl groups and alkoxy groups may optionally be substituted with one or more substituents independently selected from 1–5 halogen atoms, a phenyl group, or a mixture of these. The phenyl group, if present, may optionally be substituted with 1–3 substituents independently selected from halogen, —$CH_3$, —$CF_3$, —$OCH_3$ and —$OCF_3$. In these compounds, and as defined in general throughout this application, the alkyl groups and the alkyl portions of Oalkyl groups may be linear or branched and may optionally be cycloalkyl or may include a cycloalkyl group in their structure. For examples of prodrug structures related to those shown below, see D. N. Srinivasta et al., Bioorganic Chemistry 12, 118–129 (1984).

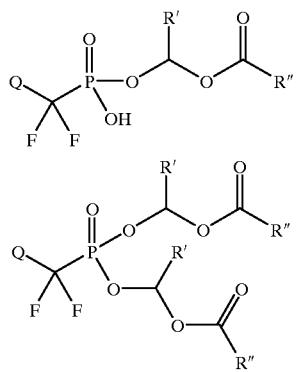

Other ester functionalities that may be used in the monoester or diester phosphonate prodrugs include phenyl esters and benzyl esters, where the phenyl ester groups have the structure —Ophenyl, and the benzyl ester groups have the structure —OCHR'phenyl, in which R' is H or $C_{1-6}$alkyl, and $C_{1-6}$alkyl is substituted as described above. In either case, phenyl is substituted as described above.

The prodrugs of this invention may therefore be defined as compounds having the formula I, in which at least one group $R^5$ is selected from the group consisting of $C_{1-6}$alkyl, phenyl, —CHR'phenyl, and —CHR'OC(=O)R", and the remaining groups $R^5$ are selected from H, $C_{1-6}$alkyl, phenyl, —CHR'phenyl and —CHR'OC(=O)R", wherein each group R' is H or $C_{1-6}$alkyl and each group R" is —$C_{1-6}$alkyl —$OC_{1-6}$alkyl, where $C_{1-6}$alkyl and the alkyl portion $OC_{1-6}$alkyl may optionally be substituted with one or more substituents independently selected from 1–5 halogen atoms, a phenyl group, or a mixture of these. The phenyl group in —CHR'phenyl, the phenyl group that is an optional substituent on $C_{1-6}$alkyl and —$OC_{1-6}$alkyl, and the phenyl ester group that is obtained when $R^5$ is phenyl may optionally be substituted with 1–3 groups independently selected from halogen, —$CH_3$, —$CF_3$, —$OCH_3$ and —$OCF_3$. By this definition, at least one of the phosphonic acid groups is a monoester or diester, and each of the remaining phosphonic acid groups, if any, may be a free acid or a monoester or diester.

In preferred compounds, the groups $R^5$ that are not H may all be the same because of the difficulty of synthesizing different $R^5$ groups on the same phosphonates. In many cases, the prodrug will be a mixture of compounds having different levels of esterification on the phosphonic acid groups because of the difficulty of synthesizing and separating a discrete pure compound.

Optical Isomers-Diastereomers-Geometric Isomers

Some of the compounds described herein contain one or more asymmetric centers and may thus give rise to diastereomers and enantiomers, which in turn can be resolved as optical isomers. The present invention includes all such diastereomers and enantiomers, including racemic mixtures and resolved, enantiomerically pure forms, and pharmaceutically acceptable salts thereof. Some of the compounds described herein contain olefinic double bonds, and unless specified otherwise, include both E and Z geometric isomers.

Salts

The pharmaceutical compositions of the present invention comprise a compound of the current invention or a pharmaceutically acceptable salt thereof as an active ingredient, and may also contain a pharmaceutically acceptable carrier and optionally other therapeutic ingredients. The term "pharmaceutically acceptable salts" refers to salts prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable acids, including inorganic and organic acids. Such acids include acetic, adipic, aspartic, 1,5-naphthalenedisulfonic, benzenesulfonic, benzoic, camphorsulfonic, citric, 1,2-ethanedisulfonic, ethanesulfonic, ethylenediaminetetraacetic, fumaric, glucoheptonic, gluconic, glutamic, hydriodic, hydrobromic, hydrochloric, isethionic, lactic, maleic, malic, mandelic, methanesulfonic, mucic, 2-naphthalenesulfonic, nitric, oxalic, pamoic, pantothenic, phosphoric, pivalic, propionic, salicylic, stearic, succinic, sulfuric, tartaric, p-toluenesulfonic acid, undecanoic, 10-undecenoic, and the like. Particularly preferred are citric, hydrobromic, hydrochloric, maleic, methanesulfonic, phosphoric, sulfuric and tartaric acids.

It will be understood that in the discussion of methods of treatment or of specific compounds which follows, references to the compounds of Formula I and other formulae are meant to include the pharmaceutically acceptable salts.

Utilities

Inhibitors of PTP-1B improve insulin-sensitivity and may have utility in preventing or treating diabetes, improving glucose tolerance and insulin-sensitivity when there is insulin-resistance, and in treating or preventing obesity, all in mammals that are in need of such treatments or that might benefit from such treatments. The compounds are more generally useful in treating Type 2 diabetes (non-insulin dependent diabetes, or NIDDM). The compounds may also cause a beneficial reduction in triglycerides and lipids.

The compound specifically exemplified herein exhibits good in vitro efficacy, having an $IC_{50}$ value of less than 1 $\mu$M in the enzyme assay described in the Assays section. The class of related compounds having Formula I is expected to also exhibit similar in vitro efficacy.

Compounds in the present class of phosphonic acids may have certain unexpected advantages. Some of the compounds may be selective in inhibiting PTP-1B in preference to T-Cell Protein Tyrosine Phosphatase (TCPTP), thus avoiding possible toxicity due to inhibition of TCPTP activity. The PTP-1B inhibitors may also have utility in treating other PTP-1B mediated diseases.

The PTP-1B inhibitors may also be useful in the treatment, prevention or control of a number of conditions that accompany type 2 diabetes, including hyperlipidemia, hypertriglyceridemia, hypercholesterolemia (including beneficially raising low HDL levels), atherosclerosis, vascular restenosis, pancreatitis, adipose cell tumors, adipose cell carcinomas such as liposarcoma, dyslipidemia, inflammatory bowel disease, inflammation in general, and other disorders where insulin resistance is a component. Finally, the compounds may be used to treat or prevent cancer, such as prostate cancer, neurodegenerative diseases and the like.

Pharmaceutical Compositions

For the treatment of any of these PTP-1B-mediated diseases the active compound may be administered orally, topically, parenterally, by inhalation spray or rectally in dosage units containing conventional pharmaceutically acceptable carriers. The term parenteral as used herein includes subcutaneous, intravenous, intramuscular and intrasternal injection and infusion techniques. In addition to the treatment of warm-blooded animals such as mice, rats, horses, cattle, sheep, dogs, cats, etc., the compounds of the invention are useful for the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. No. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxy-ethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical composition may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent, for example as a solution in 1,3-butanediol. Examples of vehicles and solvents include water, Ringer's solution and isotonic sodium chloride. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds may also be administered in the form of suppositories. These compositions can be prepared by mixing the drug with a suitable non-irritating excipient which is solid at ordinary temperatures but molten at the body temperature and will therefore release the drug. Such materials include cocoa butter and polyethylene glycols.

For topical use, creams, ointments, gels, solutions or suspensions containing the compound are employed. (For purposes of this application, topical application includes mouth washes and gargles.) Topical formulations may include cosolvents, emulsifiers, penetration enhancers, preservatives, emollients and the like.

The pharmaceutical composition may also be further comprised of a second anti-diabetic or anti-obesity effective compound.

Dose Ranges

Dosage levels on the order of from about 0.01 mg to about 100 mg/kg of body weight per day are useful in the treatment of the above-indicated conditions, or alternatively about 0.5 mg to about 7 g per patient per day. For example, the diseases and conditions described herein may be effectively treated by the administration of from about 0.01 to 50 mg of the compound per kilogram of body weight per day, or alternatively about 0.5 mg to about 3.5 g per patient per day.

The active ingredient is typically combined with the carrier to produce a dosage form suitable for the particular patient being treated and the particular mode of administration. For example, a formulation intended for the oral administration of humans may contain from about 0.5 mg to about 5 g of the active agent, compounded with an appropriate and convenient amount of carrier material which may vary from about 5 to about 95 percent of the total composition. Representative dosage forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It is understood that the specific dose level for any particular patient will depend upon a variety of factors including the age, body weight, general health, sex, diet, time of administration, route of administration, rate of excretion, drug combination and the severity of the particular disease undergoing therapy.

Combinations with Other Drugs

In further aspects, the invention encompasses pharmaceutical compositions for treating PTP-1B mediated diseases as defined above comprising an effective amount of the active compound and one or more other pharmaceutically active compounds, such as anti-diabetic compounds (for example, insulin, sulfonyl ureas, PPAR-alpha and/gamma ligands, including ligands that have both PPAR-alpha and -gamma activity), anti-obesity compounds, and compounds that improve the lipid profile of the patient.

Thus, the methods of treatment or prevention described herein may further be comprised of administering to said patient a second anti-diabetic compound in an amount effective to treat, control, or prevent diabetes, alone or in combination with the PTP-1B inhibitors of this invention.

Similarly, the methods of treatment or prevention described herein may further be comprised of administering to said patient an anti-obesity compound in an amount effective to treat, control or prevent obesity, alone or in combination with the PTP-1B inhibitors of this invention.

Similarly, the methods of treatment of diabetes may comprise the administration of a cholesterol biosynthesis inhibitor, particularly an MG-CoA reductase inhibitor, such as lovastatin, simvastatin, pravastatin, fluvastatin, atorvastatin and rivastatin, in an amount effective to improve the lipid profile. In combination with a PTP-1B inhibitor, this may be beneficial in treating or preventing atherosclerosis and other conditions that often are associated with Type 2 diabetes.

Examples of other pharmaceutically active compounds that may be combined with a compound of Formula I and administered in combination with the PTP-1B inhibitors include, but are not limited to, the following compounds or compositions or groups of compounds or compositions that are used as anti-diabetes compounds (a, b, c, d, f, and i below), anti-obesity compounds (g below), and /or compounds or compositions for lipid profile control (e and h below):

(a) insulin sensitizers including (i) PPARγ agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin;

(b) insulin or insulin mimetics;

(c) sulfonylureas such as tolbutamide and glipizide, or related materials;

(d) α-glucosidase inhibitors (such as acarbose);

(e) cholesterol lowering agents such as (i) HMG-CoA reductase inhibitors (lovastatin, simvastatin and pravastatin, fluvastatin, atorvastatin, rivastatin and other statins), (ii) sequestrants (cholestyramine, colestipol and a dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and benzafibrate), (v) inhibitors of cholesterol absorption for example beta-sitosterol and (acyl CoA:cholesterol acyltransferase) inhibitors for example melinamide and (vi) probucol;

(f) PPARα/γ agonists;

(g) antiobesity compounds such as appetite suppressants, fenfluramine, dexfenfluramine, phentiramine, sulbitramine, orlistat, neuropeptide Y5 inhibitors (NP Y5 receptor antagonosts), leptin, which is a peptidic hormone, $\beta_3$ adrenergic receptor agonists, and PPARγ antagonists and partial agonists;

(h) ileal bile acid transporter inhibitors; and (i) insulin receptor activators, such as those disclosed in copending, commonly assigned U.S. application Ser. Nos. 09/095,244 and 09/280,602.

Where a second pharmaceutical is used in addition to an active compound taught herein, the two pharmaceuticals may be administered together in a single composition, separately at approximately the same time, or on separate dosing schedules. The important feature is that their dosing schedules comprise a treatment plan in which the dosing schedules overlap in time and thus are being followed concurrently.

ASSAYS FOR DEMONSTRATING BIOLOGICAL ACTIVITY

Activity in the compounds of this application is demonstrated using the following assays for PTP-1B-inhibiting activity.

Phosphatase Assay Protocol
Materials:
EDTA -ethylenediaminetetraacetic acid (Sigma)
DMH -N,N'-dimethyl-N,N'-bis(mercaptoacetyl)-hydrazine (synthesis published in J. Org. Chem. 56, pp. 2332–2337,(1991) by R. Singh and G. M. Whitesides and can be substituted with D dithiothreitol Bistris-2,2-bis (hydroxymethyl)2,2',2" -nitrilotriethanol-(Sigma) Triton X-100-octylphenolpoly(ethylene-glycolether) 10 (Pierce)

Antibody: Anti-glutathione S-transferase rabbit (H and L) fraction (Molecular Probes)

Enzyme: Human recombinant PTP-1B, containing amino acids 1–320, fused to GST enzyme (glutathione S-transferase) or to FLAG peptide purified by affinity chromatography (Huyer et al, 1997, J. Biol. Chem., 272, 843–852). Wild type contains active site cysteine(215), whereas mutant contains active site serine(215).

Tritiated peptide: Bz-NEJJ-CONH$_2$, Mwt. 808, empirical formula, $C_{32}H_{32}T_2O_{12}P_2F_4$

| Stock Solutions | |
|---|---|
| (10X) Assay Buffer | 500 mM Bistris (Sigma), pH 6.2, MW = 209.2 |
| | 20 mM EDTA (GIBCO/BRL) |
| | Store at 4° C. |
| Prepare fresh daily: | |
| Assay Buffer (1X) (room temp.) | 50 mM Bistris |
| | 2 mM EDTA |
| | 5 mM DMH (MW = 208) |
| Enzyme Dilution | |
| Buffer (keep on ice) | 50 mM Bistris |
| | 2 mM EDTA |
| | 5 mM DMH |
| | 20% Glycerol (Sigma) |
| | 0.01 mg/ml Triton X-100 (Pierce) |
| Antibody Dilution | |
| Buffer (keep on ice) | 50 mM Bistris |
| | 2 mM EDTA |

IC$_{50}$ Binding Assay Protocol:

Compounds (ligands) which potentially inhibit the binding of a radioactive ligand to the specific phosphatase are screened in a 96-well plate format as follows:

To each well is added the following solutions @ 25° C. in the following chronological order:

1. 110 µl of assay buffer.
2. 10 µl. of 50 nM tritiated BzN-EJJ-CONH$_2$ in assay buffer (1X) @ 25° C.
3. 10 µl. of testing compound in DMSO at 10 different concentrations in serial dilution (final DMSO, about 5% v/v) in duplicate @ 25° C.
4. 10 µl. of 3.75 µg/ml purified human recombinant GST-PTP -1B in enzyme dilution buffer.
5. The plate is shaken for 2 minutes.
6. 10 µl. of 0.3 µg/ml anti-glutathione S-transferase (anti-GST) rabbit IgG (Molecular Probes) diluted in antibody dilution buffer @ 25° C.
7. The plate is shaken for 2 minutes.
8. 50 µl. of protein A-PVT SPA beads (Amersham) @ 25° C.
9. The plate is shaken for 5 minutes. The binding signal is quantified on a Microbeta 96-well plate counter.
10. The non-specific signal is defined as the enzyme-ligand binding in the absence of anti-GST antibody.
11. 100% binding activity is defined as the enzyme-ligand binding in the presence of anti-GST antibody, but in the absence of the testing ligands with the non-specific binding subtracted.
12. Percentage of inhibition is calculated accordingly.
13. IC$_{50}$ value is approximated from the non-linear regression fit with the 4-parameter/multiple sites equation (described in: "Robust Statistics", New York, Wiley, by P. J. Huber (1981) and reported in nM units.
14. Test ligands (compounds) with larger than 90% inhibition at 10 µM are defined as actives.

| Enzyme Assay PTP-1B | |
|---|---|
| Assay buffer | 50 mM Bis-Tris (pH = 6.3) |
| | 2 mM EDTA |
| | 5 mM N,N'-dimethyl-N,N'-bis(mercaptoacetyl)hydrazine (DMH) |
| Substrate | 10 mM fluorescein diphosphate (FDP) store at −20° C. |
| Enzyme dilution buffer | 50 mM Bis-Tris (pH = 6.3) |
| | 2 mM EDTA |
| | 5 mM DMH |
| | 20% (v/v) glycerol |
| | 0.01% Triton X-100 |

The assay was carried out at room temperature in 96 well plates. The reaction mixture in 170 µl contained 50 mM Bis-Tris (pH=6.3), 2 mM EDTA, 5 mM N,N'-dimethyl-N,N'bis(mercaptoacetyl)hydrazine (DMH) and 10 µM fluorescein diphosphare (FDP). 10 µl of 10 concentrations (serial dilution) of the test compound (inhibitor) dissolved in DMSO or DMSO alone for control was added to each well and the plate was mixed for 2 min. The reaction was initiated by adding 20 µl of diluted PTP-1B (50 nM in 50 mM Bis/Tris (pH=6.3), 2 mM EDTA, 5 mM DMH, 20% glycerol and 0.01% Triton X-100. The phosphatase activity was followed by monitoring the appearance of the fluorescent product fluorescein monophosphate (FMP) continuously for 15–30 min, using the Cytofluor II plate reader (PerSeptive Biosystems Inc.) with excitation of 440 nm (slit width 20 nm) and emission at 530 nm (slit width 25 nm). All the assays were done at least in duplicate. The initial rate of FMP formation is plotted against the concentration of inhibitor and the data was fitted to 4-parameter equation and the inflection point of the fit is the $IC_{50}$.

PHARMACOKINETICS IN RATS

Per Os Pharmacokinetics in Rats

PROCEDURE:

The animals are housed, fed and cared for according to the Guidelines of the Canadian Council on Animal Care.

Male Sprague Dawley rats (325–375 g) are fasted overnight prior to each PO blood level study.

The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3" gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed.

Typical time points for determination of rat blood levels after PO dosing are:

0, 15min, 30min, 1h, 2h, 4h, 6h

After the 4 hr time point bleed, food is provided to the rats ad libitum. Water is provided at all times during the study.

Vehicles:

The following vehicles may be used in PO rat blood level determinations:

| PEG 200/300/400: | restricted to 2 mL/kg |
| Methocel 0.5%–1.0%: | 10 mL/kg |
| Tween 80: | 10 mL/kg |

Compounds for PO blood levels can be in suspension form. For better dissolution, the solution can be placed in a sonicator for approximately 5 minutes.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv \text{ (mg/kg)}}{AUCiv}$$

The units of CL are mL/h·kg (milliliters per hour kilogram)

Intravenous Pharmacokinetics in Rats

PROCEDURE:

The animals are housed, fed and cared for according to the Guidelines of the Canadian Council on Animal Care.

Male Sprague Dawley (325–375 g) rats are placed in plastic shoe box cages with a suspended floor, cage top, water bottle and food.

The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they have lost their righting reflex. The rat is then placed on a restraining board, a nose cone with $CO_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone is removed. The time is noted. This constitutes the zero time point.

The 5 min bleed is taken by nicking a piece (1–2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick the tail again. The tail is cleaned with a piece of gauze and bled, as described above, into the appropriate labelled tubes.

Typical time points for determination of rat blood levels after I.V. dosing are either:

0, 5 min, 15min, 30min, 1h, 2h, 6h or 0, 5 min, 30min, 1h, 2h, 4h, 6h.

Vehicles:

The following vehicles may be used in IV rat blood level determinations:

Dextrose: 1 mL/kg

2-Hydroxypropyl-b-cyclodextrin 1 mL/kg

DMSO (dimethylsulfoxide): Restricted to a dose volume of 0.1 mL per animal

PEG 200: Not more than 60% mixed with 40% sterile water -1 mL/kg

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv \text{ (mg/kg)}}{AUCiv}$$

The units of CL are mL/h·kg (milliliters per hour kilogram).

PTP 1B INTACT CELL ASSAY

This assay is the subject of copending, commonly assigned U.S. Provisional Application No. 60/123,243, filed Mar. 8, 1999, which patent application is incorporated herein by reference, and was recently published in Cromlish, Wanda A., Paul Payette and Brian P. Kennedy (1999) *Biochem Phannocol* 58:1539–1546.

Construction of Recombinant Baculovirus Transfer Vectors And Insect Cells

Briefly, using the Bac-to-Bac Baculovirus Expression System (Gibco-BRL, Mississauga, Ontario, Canada) PTP 1B cDNA (obtained from Dr. R. L. Erikson, Harvard University, USA), is cloned into the pFASTBAC donor plasmid engineered to include a FLAG sequence at the 5' end of the cDNA (PTP1B-FL). The recombinant plasmid is transformed into competent DH10BAC *E. Coli* cells. Following transposition and antibiotic selection, the recombinant bacmid DNA is isolated from selected *E. Coli* colonies and used to transfect sf9 insect cells (Invitrogen, San Diego, Calif., U.S.A.). The sf9 cells are cultured in spinner flasks at 28° C. in Graces supplemented medium (Gibco-BRL, Mississauga, Ontario, Canada) with 10% heat-inactivated fetal bovine serum (Gibco-BRL) following the protocol of Summers and Smith (*A manual for Methods for Baculovirus Vectors and Insect Culture Procedures* (Bulletin No. 1555). Texas A & M University, Texas Agricultural Experiment Station, College Station, TX, 1987).

Intact Cell Assay

Infected sf9 cells expressing PTP1B-FL and mock infected cells, are harvested at 29 hpi (hours post infection) by gentle centrifugation (Beckman GS-6R) at 460 rpm, (48 g) for 5 min. Cells are washed once in assay buffer (Hanks' solution buffered with 15 mM Hepes, pH 7.4, obtained from Sigma, St. Louis, Mo., U.S.A.) and recentrifuged at 300 rpm (21 g) for 10 min. The cells are then gently resuspended in assay buffer and examined using a hemacytometer for cell density and viability by trypan blue exclusion. Assays are performed using a Tomtec Quadra 96 pipeting robot, programmed to mix the cells gently after each addition. In 200 µL of assay buffer, 2×10⁵ PTP expressing cells or mock infected cells are dispensed into each well of 96-well polypropylene plates and pre-incubated either with a test compound or DMSO vehicle (3 µL), for 15 min at 37 C. The pre-incubated cells are challenged with a final concentration of 10 mM pNPP (p-nitrophenyl phosphate, obtained from Sigma-Aldrich Canada Ltd., Oakville, Ontario) for 15 min, centrifuged at 4° C. and the amount of substrate hydrolysis is determined spectrophotometerically at $OD_{405}$.

Oral Glucose Tolerance Test

Oral glucose tolerance tests are done on conscious Zucker obese fa/fa rats or obese ob/ob mice (age 12 weeks or older). The animals are fasted for 16–18 hours before use for experiments. A test compound or a vehicle is given either intraperitoneally or orally 60 minutes before oral administration of a glucose solution at a dose of 2 g/kg body weight. Blood glucose levels are measured using a Medisense glucometer from tail bled samples taken at different time points before and after administration of glucose. A time curve of the blood glucose levels is generated and the area-under-the-curve (AUC) for 120 minutes is calculated (the time of glucose administration being time zero). Percent inhibition is determined using the AUC in the vehicle-control group as zero percent inhibition.

In separate studies, C57BL/6J mice are fed a high fat (35%) and high carbohydrate (36%) diet obtained from Bioserv (Frenchtown, N.J.) for 3 to 4 weeks, at which time the mice gained 50–100% of the baseline body weight. Oral glucose tolerance tests are done in the same manner as described above.

EXAMPLES

The invention is further illustrated by the following non-limiting example. The new compound according to this invention is summarized in Table 1. Methods used to synthesize the compound are summarized under the title, Methods of Synthesis. Specific intermediates and methods of making them are presented in the Synthesis of Intermediates section. Finally, the actual synthesis of the compound is presented in Example 1. In the various synthetic examples:

(i) all operations were carried out at room or ambient temperature, that is, at a temperature in the range 18–25° C., (ii) evaporation of solvent was carried out using a rotary evaporator under reduced pressure (600–4000 pascals: 4.5–30 mm. Hg) with a bath temperature of up to 60° C., (iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta ($\delta$) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (litre(s)), mL (millilitres), g (gram (s)), mg (milligrams(s)), mol (moles), mmol (millimoles), eq (equivalent(s)).

Table of Examples

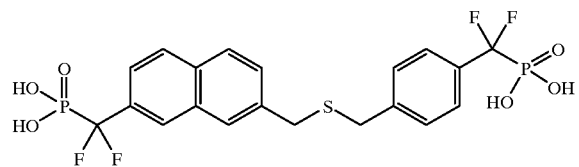

METHODS OF SYNTHESIS

The compounds of the present invention can be prepared according to the following methods.

METHOD A

An appropriately substituted aniline 1, from commercial sources or prepared from readily available starting material, is diazotized and converted to the corresponding cyano intermediate 2 under Sandmyer's condition. Compound 2 is then reduced with DIBAL-H from −78° C. to room temperature to give the hydroxymethyl benzaldehyde 3. The hydroxyl group of 3 is converted to the bromo group by the treatment with a brominating mixture such as $POBr_3$ and DMF to give bromide 4. The aldehyde of 4 is reacted with an anion derived from dialkyl phosphite and a base such as $LiN(TMS)_2$ to afford the hydroxy intermediate 5. Oxidation of 5 with $MnO_2$ or under Swern's condition provides the ketophosphonate 6. Treatment with DAST then gives bromide 7. Bromide 7 is then reacted with potassium thioacetate to give thioacetate 8, which is hydrolysed with a base to provide thiol 9.

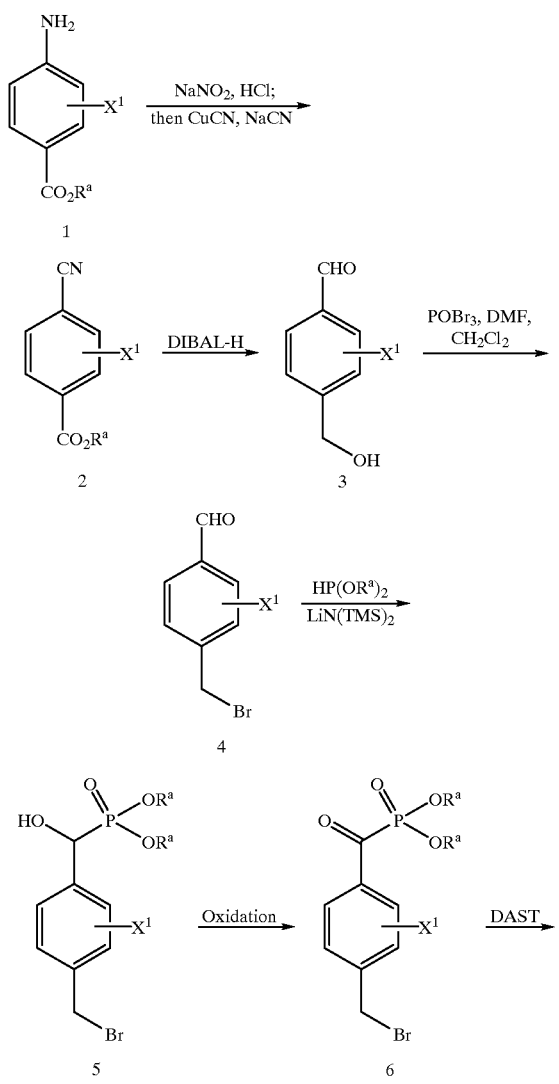

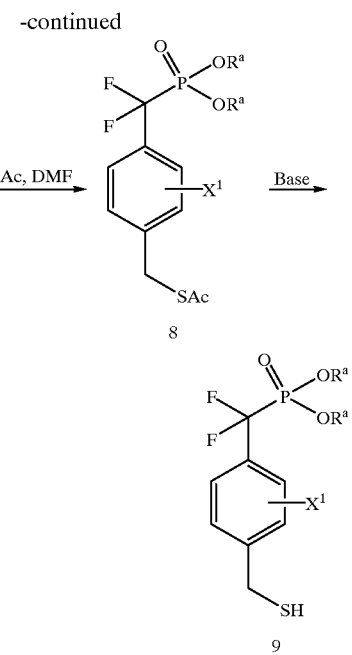

$R^a$ is a substituent, which is part of an ester group, and can be selected independently.

METHOD B

Naphthalene-2-7-diol 10 can be converted to the corresponding bis-triflate 11 readily. Palladium catalyzed carboxylation of 11 gives the diester 12. Reduction of the diester 12 with DIBAL-H gives the corresponding diol 13. Mono-protection of the diol with TBDMSCl followed by oxidation of the remaining alcohol with MnO2 gives the aldehyde 15. Deprotection of the silyl-ether of 15 with TBAF gives the alcohol 16 which can be mesylated with MsCl to give compound 17. Reaction of the mesylate 17 with the thiol 9 (prepared according to Method A) under basic condition gives the phosphonate 18. Reaction of the aldehyde of 18 with lithium diethylphosphite gives the hydroxy-phosphonate 19 which can be oxidized to the corresponding keto-phosphonate 20. Reaction of the keto-phosphonate 20 with DAST gives the bis-difluoro-methyl phosphonate 21. Deprotection of the phosphonate with TMSBr gives the bis phosphonic acid 22.

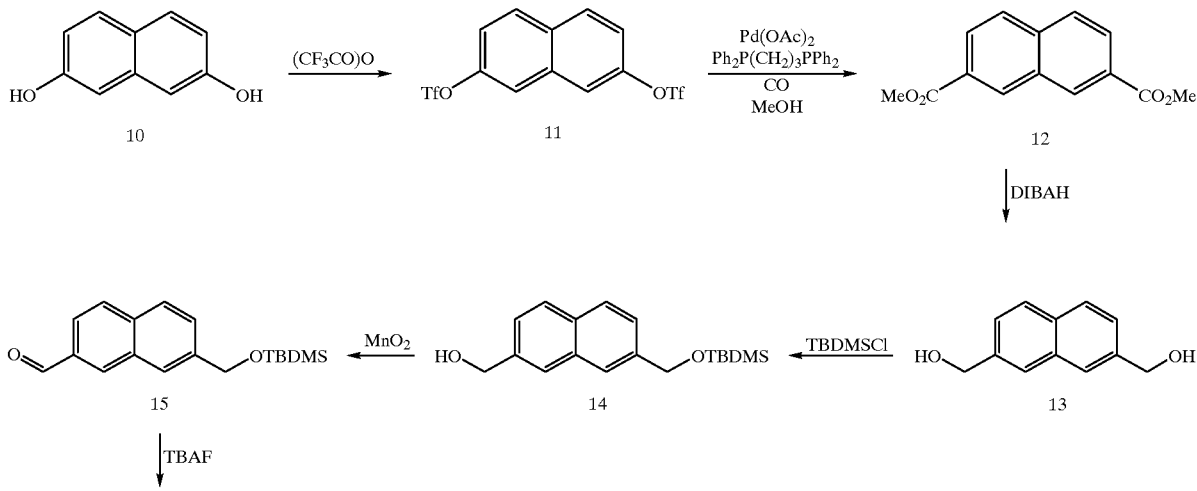

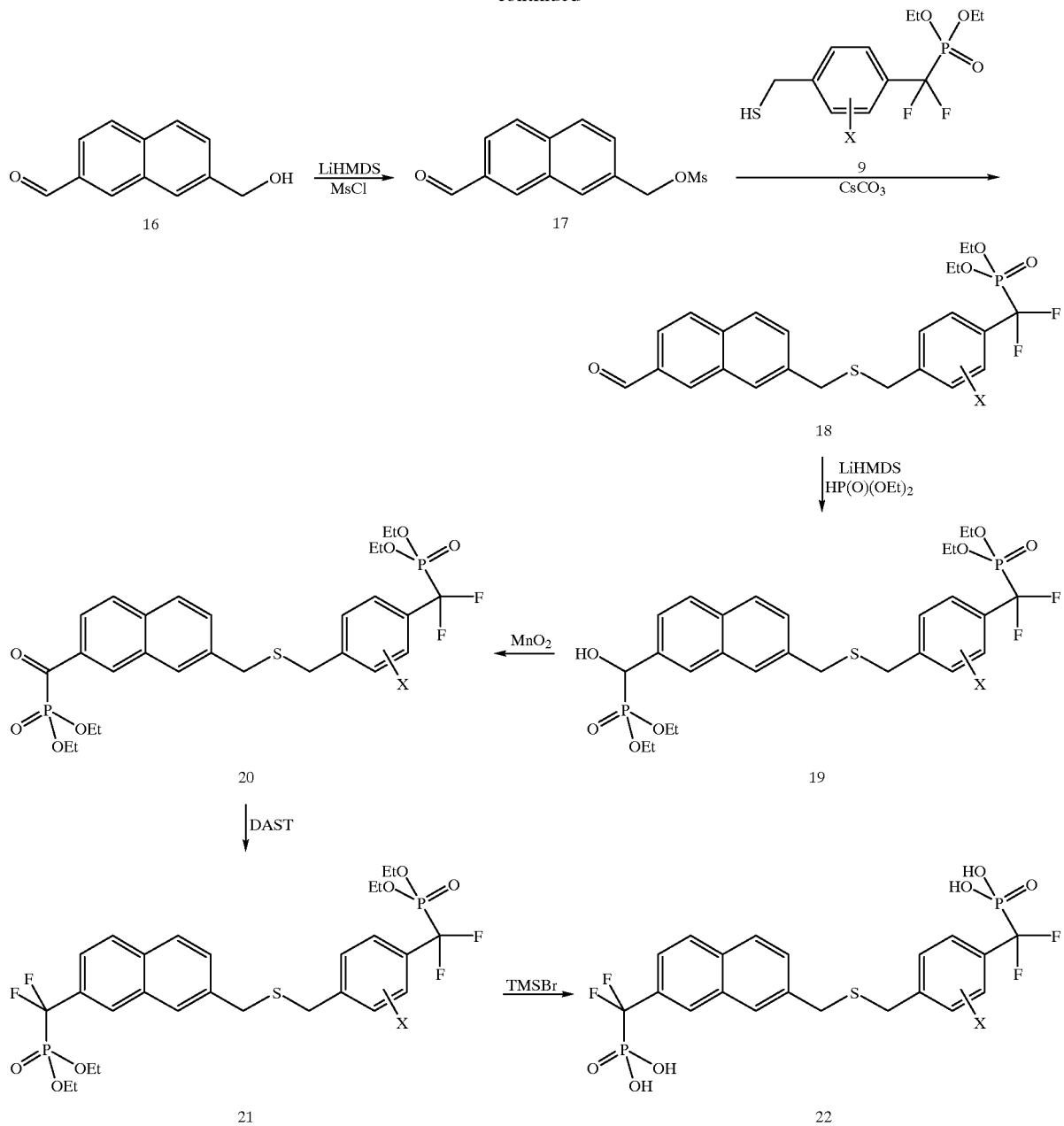

SYNTHESIS OF INTERMEDIATES FOR THE USE IN SYNTHETIC EXAMPLES

Difluoro-(4-mercaptomethyl-phenyl)-methyl-phosphonic acid diethyl ester

To a cold (0° C.) degassed DMF solution (100 mL) of (4-bromomethylphenyl)difluoromethylphosphonic diethyl ester (20 mmol., 7.14 g) was added potassium thioacetate (22 mmol., 2.5 g.). The mixture was stirred 1 hour at 0° C. and 1 hour at 25° C. It was cooled again at 0° C. and hydrazine monohydrate (25 mmol., 1.25 g.) was added. The mixture was stirred at 25° C. for 1 hour. It was poured on ice, dilute HCl and diethyl ether. The organic layer was separated and the aqueous further extracted with diethyl ether. The organic layers were combined and washed with brine and dried with magnesium sulfate. Removal of the solvent left a residue (6.1 g.) wich was passed on a short bed of silica eluting with ethyl acetate and hexanes (1:1) to yield the title compound (5.6 g.).

$^1$H NMR (Acetone-d$_6$) δ7.45–7.55 (4H, m), 4.05–4.25 (4H, m), 3.75–3.85 (2H, d), 2.25–2.35 (1H, t), 1.2–1.3 (6H, m).

Example

Example 1

{7-[4-(Difluoro-phosphono-methyl)-benzylsulfanyl-methyl]-naphthalen-2-yl}-difluoromethyl-phosphonic acid Step 1: Trifluoro-methanesulfonic acid 7-(trifluoro-methanesulfonyloxy)-naphthalene-2-yl ester To a cold (−78° C.) mixture of naphthalene-2-7-diol (5.4 g, 33.8 mmol), 2,6-lutidine (8.0 g) and DMAP (824 mg) in THF (60 mL) and CH$_2$Cl$_2$ (60 mL) was added trifluoromethanesulfonic anhydride (20 g). The mixture was stirred at −78° C. for 1.5 h. and then warmed to 0° C.

Aqueous NaHCO$_3$ was added, and the mixture was extracted with CH$_2$Cl$_2$. The combined organic extracts were washed with brine, dried (anhyd. MgSO$_4$) and concentrated in vacuo. The residue was purified by chromatography on silica gel and the product was isolated by recrystallization in EtOAc/Hexane to give 6 g (42%) of the title compound.

Step 2: Naphthalene-2-7-dicarboxylic acid dimethyl ester

A mixture of the product of step 1 (6.07 g, 14.3 mmol), Pd(OAc)$_2$ (390 mg, 1.74 mmol) and Ph$_2$P(CH$_2$)$_3$PPh$_2$ (720 mg, 1.74 mmol), was degassed and recharged 3 times with CO. MeOH (17.7 mL, 436 mol), NEt$_3$ (7.3 mL, 52.3 mmol), and DMSO (58 mL) was added. The mixture was heated to 70° C. for 5 h. Aqueous NH$_4$Cl was added, and the mixture was extracted with EtOAc. The combined organic extracts were washed with brine, dried (anhyd. MgSO$_4$) and concentrated in vacuo. The residue was purified by chromatography on silica gel and the product was isolated by recrystallization in EtOAc/Hexane to give 1.82 g (52%) of the title compound.

Step 3: (7-Hydroxymethyl-naphthalen-2-yl)-methanol

To a cold (-78° C.) solution of the product of step 2 (1.82 g, 7.46 mmol) in THF (50 mL) was added diisobutylaluminum hydride (37 mL, 1M in hexane). The mixture was stirred at −78° C. for 1.75 h. H$_2$SO$_4$ (2N) was added and the mixture was extracted with EtOAc. The combined organic extracts were washed with brine, dried (anhyd. MgSO$_4$) and concentrated in vacuo. The residue was purified by chromatography on silica gel to give 950 mg (68%) of the title compound.

Step 4: (7-(tert-Butyl-dimethyl-siloxy)methyl-naphthalen-2-yl)-methanol

To a cold (0° C.) solution of the product of step 3 (986 mg, 5.24 mmol) in THF (26 mL) was added LiHMDS (5.24 mL, 1.0 M in THF), TBDMSiCl (790 mg, 5.24 mmol) and DMAP (640 mg, 5.24 mmol). The mixture was then stirred at rt for 2 h. Aqueous NH$_4$Cl was added, and the mixture was extracted with EtOAc. The combined organic extracts were washed with brine, dried (anhyd. MgSO$_4$) and concentrated in vacuo. The residue was purified by chromatography on silica gel to give 868 mg (55%) of the title compound.

Step 5: (7-(tert-Butyl-dimethyl-siloxv)methyl-naphthalene-2-carbaldehyde

To a solution of the product of step 4 (868 mg, 2.88 mmol) in acetone (15 mL) was added MnO$_2$ (1.5 g, 17.25 mmol). The mixture was stirred at rt for 2.5 h and then filtered through celite. The filtrate was concentrated in vacuo. The residue was purified by chromatography on silica gel to give 727 mg (84%) of the title compound.

Step 6: 7-Hydroxymethyl-naphthalene-2-carbaldehyde

To a solution of the product of step 5 (727 mg, 2.42 mmol) in THF (5 mL) was added a solution of TBAF (2.9 mL, 1.0 M in THF). The mixture was stirred at rt for 0.75 h. The mixture was concentrated in vacuo. The residue was purified by chromatography on silica gel to give 430 mg (95%) of the title compound.

Step 7: Methanesulfonic acid 7-formyl-naphthalen-2-ylmethyl ester

To a cold (0° C.) solution of the product of step 6 (430 mg, 2.31 mmol) in CH$_2$Cl$_2$ (5 mL) was added MsCl (318 mg, 2.7 mmol) and Et$_3$N (559 mg, 5.5 mmol). The mixture was stirred at 0° C. for 2 h. Aqueous NH4Cl was added, and the mixture was extracted with EtOAc. The combined organic extracts were washed with brine, dried (anhyd. MgSO$_4$) and concentrated in vacuo. The crude product was used in the next step without further purification.

Step 8: Difluoro-F4-(7-formyl-naphthalen-2-ylmethylsulfanyl-methyl)-phenyl]-methyl-phosphonic acid diethyl ester To a cold (0° C.), degassed, solution of the product of step 7 (2.31 mmol) in DMF (15 mL) was added CsCO$_3$ (6.93 mmol) and difluro-(4-mercaptomethyl-phenyl)-methyl-phosponic acid diethyl ester (787 mg, 2.5 mmol). The mixture was then stirred at rt for 1.5 h. H$_2$O was added, and the mixture was extracted with EtOAc. The combined organic extracts were washed with brine, dried (anhyd. MgSO$_4$) and concentrated in vacuo. The residue was purified by chromatography on silica gel to give 946 mg (86%) of the title compound.

Step 9: {7- { 4- [(Diethoxy-phosphoryl)-difluoro-methyl]-benzylsulfanyl-methyl } -naphthalen-2-yl } -hydroxymethyl-phosphonic acid diethyl ester To a cold (−78° C.), degassed, solution of diethylphosphite (327 mg, 2.37 mmol) in THF (10 mL), was added LiHMDS (2.4 mmol, 1.0 M in THF). The mixture was stirred at −78° C. for 0.25 h. A solution of the product from step 8 (946 mg, 1.98 mmol) in THF (7 mL) was added. The mixture was stirred at −78° C. for 0.5 h then warmed to rt for 0.5 h. Aqueous NH$_4$Cl was added, and the mixture was extracted with EtOAc. The combined organic extracts were washed with brine, dried (anhyd. MgSO$_4$) and concentrated in vacuo. The residue was purified by chromatography on silica gel to give 979 mg (80%) of the title compound.

Step 10: {7- { 4-[(Diethoxy-phosphoryl)-difluoro-methyl]-benzylsulfanyl-methyl} -naphthalen-2-carbonyl-phosphonic acid diethyl ester To a solution of the product of step 9(200 mg, 0.32 mmol) in acetone (15 mL) was added MnO$_2$ (422 mg, 4.8 mmol). The mixture was stirred at rt for 2.5 h and then filtered through celite. The filtrate was concentrated in vacuo. The residue was redissolved in EtOAc. Aqueous NH$_4$Cl was added, and the mixture was extracted with EtOAc. The combined organic extracts were washed with brine, dried (anhyd. MgSO$_4$) and concentrated in vacuo. The crude product was used in the next step without further purification.

Step 11: {7-{4-[(Diethoxy-phosphoryl)-difluoro-methyl]-benzylsulfanyl-methyl}-naphthalen-2-yl}-difluoro-methyl-phosphonic acid diethyl ester To a cold (−20° C.) solution of of the product of step 10 in CHCl$_3$(10 mL), was added dropwise DAST (0.376 mL, 3.0 mmol). The mixture was warmed to rt very slowly and stirred at rt for 20 h. The mixture was then added slowly to a mixture of ice-aqueous NH4OH and extracted with CH$_2$Cl$_2$. The combined organic extracts were washed with brine, dried (anhyd. MgSO$_4$) and concentrated in vacuo. The residue was purified by chromatography on silica gel to give 45 mg (22%) of the title compound.

Step 12: {7-[4-(Difluoro-phosphono-methyl)-benzylsulfanyl-methyl]-naphthalen-2-yl }-difluoromethyl-phosphonic acid To a solution of the product of step 11(45 mg, 0.07 mmol) in CHCl$_3$ (2 mL) was added TMSBr (0.1 mL). The mixture was stirred at rt for 20 h. The solution was concentrated in vacuo. EtOH (2 mL) was added, and the mixture was stirred at rt for 0.5 h. Concentration of the EtOH solution in vacuo gave (27 mg, 74%) of the title compound.

$^1$H NMR (Acetone-d6) δ3.69 (s, 2 H), 3.85 (s, 2 H), 7.37 (d, 2 H), 7.50 (d, 2 H), 7.61 (q, 2 H), 7.74 (s, 1 H) 7.91 (d, 1 H), 7.96 (d, 1 H), 8.09 s (1 H).

What is claimed is:

1. A compound represented by formula I:

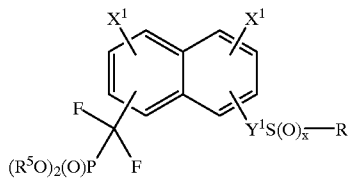

or a pharmaceutically acceptable salt or prodrug thereof, wherein:

Each $X^1$ is independently selected from the group consisting of: H, OH, halogen, CN, $CO_2H$, $CO_2C_{1-6}$alkyl, $CO_2C_{2-6}$alkenyl, $OC_{1-6}$alkyl, $OC_{2-6}$alkenyl, $C(O)C_{1-6}$alkyl, $C(O)C_{2-6}$alkenyl, $OC(O)C_{1-6}$alkyl, $OC(O)C_{2-6}$alkenyl, $S(O)_xC_{1-6}$alkyl, $S(O)_xC_{2-6}$alkenyl, $C_{1-6}$ alkyl, $C_{2-6}$alkenyl, $S(O)_2NR^1R^2$, $C(O)NR^1R^2$, and $NR^1R^2$, wherein each alkyl group and each alkenyl group in each substituent is optionally substituted with one or more groups independently selected from (a) 1–13 halogen atoms and (b) 1–2 substituents independently selected from $OC_{1-3}$ alkyl, $C(O)C_{1-3}$alkyl, $OC(O)C_{1-3}$ alkyl, $CO_2H$, and $CO_2C_{1-3}$alkyl;

$X^1$, $CF_2P(O)(OR^5)_2$ and $Y^1S(O)_xR$ are substituted onto any position of either ring;

Each x is independently 0, 1, or 2;

$R^5$ is H;

$R^1$ and $R^2$ are each independently selected from the group consisting of H and $C_{1-4}$alkyl, wherein said alkyl substituents are optionally substituted with 1–9 halogen atoms;

Each halogen is independently selected from I, Cl, Br and F;

$Y^1$ is selected from the group consisting of a bond, a $C_{1-4}$ alkylene group, and a $C_{2-4}$ alkenylene group, wherein said alkylene group and said alkenylene group are optionally substituted with one or more groups selected from (a) 1–8 halogen atoms, and (b) 1–2 substituents independently selected from OH and $OC_{1-4}$ alkyl, said $OC_{1-4}$ alkyl being optionally substituted with 1–9 halogen atoms;

R is selected from the group consisting of $C_{1-10}$ alkyl, $C_{2-10}$alkenyl, $C_{2-10}$alkadienyl, $C_{2-10}$alkynyl, $Ar^1$, and $Het^1$, wherein said alkyl, alkenyl, alkadienyl, and alkynyl are optionally substituted with one substituent selected from $Ar^1$ and $Het^1$, and are optionally also substituted with one or more groups independently selected from (a) 1–21 halogen atoms, and (b) 1–2 substituents independently selected from OH, CN, $CO_2H$, $CO_2C_{1-6}$ alkyl, $CO_2C_{2-6}$ alkenyl, $OC_{1-6}$alkyl, $OC_{2-6}$ alkenyl, $OC(O)C_{1-6}$alkyl, $OC(O)C_{2-6}$alkenyl, $C(O)C_{1-6}$alkyl, $C(O)C_{2-6}$alkenyl, C(O)Aryl, OC(O) Aryl, OAryl, $CO_2$Aryl, $S(O)_xC_{1-6}$alkyl, $S(O)_xC_{2-6}$ alkenyl, $S(O)_2NR^1R^2$, $C(O)NR^1R^2$, and $NR^1R^2$, wherein said alkyl groups and said alkenyl groups of said substituents are optionally substituted with 1–13 halogen atoms;

$Het^1$ is a 5–10 membered aromatic ring system comprising 1 ring or 2 rings fused together and 1–4 heteroatoms selected from O, N, $S(O)_x$, and combinations thereof, and 0–2 carbonyl groups, wherein one of said fused rings is optionally a benzene ring, and said $Het^1$ is optionally substituted with one or more groups independently selected from (a) one group selected from $CF_2P(O)(OR^5)_2$, $CO_2H$, $CF_2CO_2H$, $P(O)(OR^5)_2$, and $SO_2R^4$, and (b) 1–2 groups independently selected from R3;

$Ar^1$ is phenyl or naphthyl, optionally substituted with one or more groups independently selected from (a) one group selected from $CF_2P(O)(OR^5)_2$, $CO_2H$, $CF_2CO_2H$, $P(O)(OR^5)2$, $SO_2R^4$, and $Ar^2$, and (b) 1–2 groups selected from $R^3$;

$Ar^2$ is phenyl, naphthyl or a 5–10 membered aromatic ring system comprising 1 ring or 2 rings fused together and 1–4 heteroatoms selected from O, N, $S(O)_x$, and combinations thereof, and 0–2 carbonyl groups, wherein one of said fused rings is optionally a benzene ring, wherein $Ar^2$ is optionally substituted with one or more groups independently selected from (a) one group selected from $CF_2P(O)(OR^5)_2$, $CO_2H$, $CF_2CO_2H$, $P(O)(OR^5)_2$, and $SO_2R^4$, and (b) 1–2 groups selected from $R^3$;

$R^3$ is selected from the group consisting of halogen, OH, CN, $CO_2H$, $CO_2C_{1-10}$ alkyl, $CO_2C_{2-10}$ alkenyl, $OC_{1-10}$alkyl, $OC_{2-10}$ alkenyl, $C_{1-10}$alkyl, $C_{2-10}$ alkenyl, $OC(O)C_{1-10}$alkyl, $OC(O)C_{2-10}$alkenyl, $C(O)C_{1-10}$alkyl, $C(O)C_{2-10}$alkenyl, C(O)Aryl, OC(O)Aryl, OAryl, $CO_2$Aryl, $S(O)_xC_{1-10}$alkyl, $S(O)_xC_{2-10}$alkenyl, $S(O)_2NR^1R^2$, $C(O)NR^1R^2$, $NR^1R^2$, Aryl, and Het, wherein each alkyl group and each alkenyl group of each substituent is optionally substituted with one or more groups independently selected from (a) 1–21 halogen atoms and (b) 1–2 substituents independently selected from OH, $OC_{1-3}$ alkyl, $CO_2H$, $CO_2C_{1-3}$alkyl, $C(O)C_{1-3}$ alkyl, $OC(O)C_{1-3}$alkyl, and phenyl, wherein said phenyl is optionally substituted with 1–3 substituents independently selected from $OCH_3$, $OCF_3$, Cl and F, and said $C_{1-3}$ alkyl groups of said substituents are optionally substituted with one or more groups independently selected from (a) 1–7 halogen atoms and (b) 1–2 phenyls, wherein said phenyls are optionally substituted with 1–3 halogen atoms;

Aryl is a 6–14 membered aromatic carbocyclic moiety comprising 1 ring or 2–3 fused rings, wherein said Aryl is optionally substituted with 1–3 substituents independently selected from $C_{1-3}$alkyl, halogen, $OC_{1-3}$ alkyl, $C(O)C_{1-3}$ alkyl, $OC(O)C_{1-3}$alkyl, $CO_2H$, and $CO_2C_{1-3}$ alkyl, wherein said alkyl groups in said substituents are optionally substituted with 1–7 halogen atoms;

Het is a 5–10 membered aromatic ring system comprising 1–4 heteroatoms selected from N, $S(O)_x$, O, and mixtures thereof, and 0–2 carbonyl groups, wherein said Het comprises 1 ring or 2 fused rings, one of which fused rings may be a benzene ring, and said Het is optionally substituted with 1–3 substituents independently selected from $C_{1-3}$alkyl, halogen, $OC_{1-3}$ alkyl, $C(O)C_{1-3}$alkyl, $OC(O)C_{1-3}$alkyl, $CO_2H$, and $CO_2C_{1-3}$ alkyl, wherein said alkyl groups are optionally substituted with 1–7 halogen atoms;

Alkyl, alkenyl, alkadienyl and alkynyl are linear, branched or cyclic hydrocarbon structures, or combinations thereof containing the indicated number of carbon atoms and substituted as indicated, wherein said alkyl, alkenyl, alkadienyl and alkynyl respectively are saturated, comprise one double bond, comprise 2 double bonds, or comprise one triple bond; and $R^4$ is phenyl or $C_{1-4}$ alkyl, wherein said phenyl is optionally substituted with one or more groups independently selected from (a) 1–3 halogen atoms and (b) 1–2 $C_{1-3}$ alkyl or $C_{1-3}$alkoxy groups, which are optionally substituted with 1–7 halogen atoms, and said $C_{1-4}$ alkyl is optionally substituted with one or more groups independently selected from (a) 1–9 halogen atoms and (b) 1–2 $C_{1-3}$ alkoxy groups, which are optionally substituted with 1–7 halogen atoms.

2. The compound as recited in claim 1, wherein said halogen atom substituents are independently selected from Cl, Br, and F.

3. The compound as recited in claim 1, wherein one group $X^1$ is H, and the second group $X^1$ is selected from the group consisting of a halogen atom, $CH_3$, $OCH_3$, OH and $CO_2H$.

4. The compound as recited in claim 1, wherein one group $X^1$ is H; the second group $X^1$ is selected from the group consisting of Cl, F, and Br; and the $Y^1$ substituent and the group $CF_2$ $P(O)(OR^5)_2$ are on different rings of Formula I.

5. The compound as recited in claim 4, wherein one group $X^1$ is Br and is on a carbon adjacent to the carbon to which $CF_2$ $P(O)(OR^5)_2$ is attached.

6. The compound as recited in claim 5, wherein $Y^1S(O)_xR$ and $CF_2P(O)(OR^5)_2$ are attached to the 2,7-positions of the naphthalene ring.

7. The compound as recited in claim 1, wherein $Y^1$ is a bond, $CH_2$, or linear $C_{2-4}$alkyl.

8. The compound as recited in claim 1, wherein:
the first two carbons of $Y^1$ starting from S may be linear or monobranched, and
the first two carbons of R starting from S may be linear or monobranched.

9. The compound as recited in claim 1, wherein $Y^1$ is selected from the group consisting of a linear $C_{1-4}$ alkylene group and a linear $C_{1-4}$ alkenylene group and is optionally substituted with one or more groups independently selected from (a) 1–8 halogen atoms, and (b) 1–2 substituents independently selected from OH and $OC_{1-4}$ alkyl, said $OC_{1-4}$ alkyl being optionally substituted with 1–9 halogen atoms;
and R is selected from the group consisting of a linear $C_{1-10}$ alkyl, linear $C_{2-10}$alkenyl, linear $C_{2-10}$alkadienyl, and linear $C_{2-10}$alkynyl, wherein R is substituted with $Ar^1$ or $Het^1$, and R is optionally also substituted with one or more groups independently selected from (a) 1–21 halogen atoms, and (b) 1–2 substituents independently selected from OH, CN, $CO_2H$, $CO_2C_{1-6}$ alkyl, $CO_2C_{2-6}$ alkenyl, $OC_{1-6}$alkyl, $OC_{2-6}$ alkenyl, OC(O)$C_{1-6}$alkyl, OC(O)$C_{2-6}$alkenyl, C(O)$C_{1-6}$alkyl, C(O)$C_{2-6}$ alkenyl, C(O)Aryl, OC(O)Aryl, OAryl, $CO_2$Aryl, $S(O)_x$ $C_{1-6}$alkyl, $S(O)_xC_{2-6}$alkenyl, $S(O)_2NR^1R^2$, C(O)$NR^1R^2$, and $NR^1R^2$, wherein said alkyl groups and said alkenyl groups of said substituents are optionally substituted with 1–13 halogen atoms.

10. The compound as recited in claim 1, wherein R is selected from the group consisting of $C_{1-4}$ alkyl and $C_{1-4}$ alkenyl and is substituted with $Ar^1$; wherein $Ar^1$ is phenyl or naphthyl optionally substituted with $CF_2P(O)(OR^5)_2$ and optionally also substituted with 1–2 $R^3$, where $R^3$ is selected from the group consisting of Br, Cl, F, OH, and $C_{1-3}$ alkyl.

11. The compound as recited in claim 10, wherein $R^3$ is Br.

12. The compound as recited in claim 1, wherein R is selected from the group consisting of $C_{1-4}$ alkyl and $C_{1-4}$ alkenyl, and is substituted with $Ar^1$;

$Ar^1$ is phenyl or naphthyl and is substituted with $Ar^2$;

$Ar_2$ is a 5–10 membered aromatic ring system comprising 1 ring or 2 rings fused together and 1–4 heteroatoms selected from 0, N, $S(O)_x$, and combinations thereof, and 0–2 carbonyl groups, wherein one of said fused rings is optionally a benzene ring, and $Ar^2$ is optionally substituted with (a) $P(O)(OH)_2$ or $CO2H$ and (b) 1–2 groups $R^3$;

$R^3$ is selected from $C_{1-10}$ alkyl, $OC_{1-10}$ alkyl, C(O)Aryl, and Aryl, where said $C_{1-10}$ alkyl and $OC_{1-10}$ alkyl are optionally substituted with 1–2 substituents independently selected from $OC_{1-3}$ alkyl, phenyl, and $CO2H$; and $X^1$, $X^2$, $R^1$, $R^2$, $R^4$, $R^5$, x, $Y^1$, Aryl, Het, and $Het^1$ are as defined in claim 1.

13. The compound as recited in claim 12, wherein $Ar^2$ is quinoline.

14. The compound as recited in claim 1, wherein R is selected from the group consisting of 4 alkyl and 4 alkenyl and is substituted with $Ar^1$;

$Ar^1$ is phenyl and is substituted with $Ar^2$;

$Ar^2$ is phenyl, and is optionally substituted with (a) one substituent selected from $P(O)(OR^5)_2$, $CO_2H$, and $SO2R^4$, and (b) 1–2 $R^3$;

$R^4$ is phenyl or $C_{1-4}$ alkyl;

$R^3$ is selected from OH, Br, $OC_{1-10}$ alkyl, $C_{1-10}$ alkyl, Aryl, and $C_{1-10}$alkenyl, where each alkyl group and each alkenyl group is optionally substituted with $OC_{1-3}$ alkyl or phenyl; and $X^1$, $X^2$, $R^1$, $R^2$, $R^5$, x, $Y^1$, Aryl, Het and $Het^1$ are as defined in claim 1.

15. A compound having the formula I as recited in claim 1, or a pharmaceutically acceptable salt thereof, wherein each group —$OR^5$ is selected from —OH and a group that is converted to —OH under physiological conditions during or after administration to a mammalian patient, thereby yielding a phosphonic acid group, or a salt thereof, wherein at least one group —$OR^5$ is not an —OH group, wherein all substituent groups other than $R^5$ are as defined in claim 1.

16. A compound as recited in claim 15, wherein one group $R^5$ is selected from $C_{1-6}$alkyl, phenyl, —CHR'phenyl and —CHR'OC(=O)R", and the remaining groups $R^5$ are independently selected from H, $C_{1-6}$alkyl, phenyl, —CHR'phenyl and —CHR'OC(=O)R", wherein each R' is H or $C^{1-6}$alkyl, and each R" -$C_{1-6}$alkyl —$OC_{1-6}$alkyl, wherein $C_{1-6}$alkyl and —$OC_{1-6}$alkyl in each occurrence are optionally substituted with one or more substituents independently selected from 1–5 halogen atoms, a phenyl group, or a mixture of these, and each phenyl in each occurrence is optionally substituted with 1–3 substituents independently selected from halogen, —$CH_3$, —$CF_3$, —$OCH_3$ and —$OCF_3$.

17. A compound in accordance with claim 1, which is {7-[4-(Difluoro-phosphono-methyl)-benzylsulfanyl-methyl]-naphthalen-2-yl}-difluoromethyl-phosphonic acid.

18. A pharmaceutical composition which is comprised of a compound in accordance with claim 1 in combination with a pharmaceutically acceptable carrier.

19. A pharmaceutical composition which comprises a first anti-diabetic or anti-obesity compound in accordance with claim 1 and a pharmaceutically acceptable carrier and which further comprises a second anti-diabetic or anti-obesity effective compound.

20. A method of treating or controlling diabetes in a mammalian patient in need of such treatment comprising administering to said patient an anti-diabetic effective amount of a compound of claim 1.

21. A method of treating or controlling obesity in a mammalian patient in need of such treatment comprising administering to said patient an anti-obesity effective amount of a compound of claim 1.

22. A method in accordance with claim 20, further comprising administering to said patient an effective amount of a compound selected from the group consisting of:
(a) insulin sensitizers, PPAR-gamma agonists, partial agonists, and antagonists, PPAR-alpha agonists, PPAR-delta agonsts, and biguanides;
(b) insulin and insulin mimetics;
(c) sulfonylureas;
(d) α-glucosidase inhibitors;
(e) cholesterol lowering agents selected from the group consisting of (i) HMG-CoA reductase inhibitors; (ii) sequestrants, (iii) nicotinyl alcohol, nicotinic acid and salts thereof, (iv) PPARα agonists, (v) inhibitors of cholesterol absorption; and (vi) probucol;
(f) PPARα/γ agonists;
(g) antiobesity compounds selected from the group consisting of appetite suppressants, fenfluramine, dexfenfluramine, phentiramine, sulbitramine, orlistat, neuropeptide Y5 inhibitors (NP Y5 receptor antagonosts), leptin, β₃ adrenergic receptor agonists, and PPARγ antagonists and partial agonists;
(h) ileal bile acid transporter inhibitors; and
(i) insulin receptor activators.

23. A method in accordance with claim 21, further comprising administering to said patient a compound selected from the group consisting of:
(a) insulin sensitizers, PPAR-gamma agonists, partial agonists, and antagonists, PPAR-alpha agonists, PPAR-delta agonsts, and biguanides;
(b) insulin and insulin mimetics;
(c) sulfonylureas;
(d) α-glucosidase inhibitors;
(e) cholesterol lowering agents selected from the group consisting of (i) HMG-CoA reductase inhibitors; (ii) sequestrants, (iii) nicotinyl alcohol, nicotinic acid and salts thereof, (iv) PPARα agonists, (v) inhibitors of cholesterol absorption; and (vi) probucol;
(f) PPARα/γ agonists;
(g) antiobesity compounds selected from the group consisting of appetite suppressants, fenfluramine, dexfenfluramine, phentiramine, sulbitramine, orlistat, neuropeptide Y5 inhibitors (NP Y5 receptor antagonosts), leptin, β₃ adrenergic receptor agonists, and PPARγ antagonists and partial agonists;
(h) ileal bile acid transporter inhibitors; and
(i) insulin receptor activators.

24. A pharmaceutical composition in accordance with claim 18 further comprising an HMG-CoA reductase inhibitor.

25. A method in accordance with claim 20, further comprising administering to said patient an effective amount of an HMG-CoA reductase inhibitor.

26. A method for treating or controlling atherosclerosis in a mammalian patient in need of such treatment comprising administering to said patient an effective amount of a compound of claim 1 and an effective amount of an HMG-CoA reductase inhibitor.

27. A method of treating or controlling one or more diseases or conditions selected from the group consisting of Type 2 diabetes, inadequate glucose tolerance, insulin resistance, obesity, said method comprising the administration of an effective amount of a compound of claim 1.

28. A method of treating or controlling one or more diseases or conditions, selected from the group consisting of Type 2 diabetes, inadequate glucose tolerance, insulin resistance, and obesity, said method comprising the administration of an effective amount of a compound of claim 1 and the administration of an effective amount of one or more pharmaceutically active compounds selected from the group consisting of an HMG-CoA reductase inhibitor, an anti-obesity agent, and an antidiabetic compound.

29. A pharmaceutical composition comprising (1) a compound of claim 1, (2) one or more pharmaceutically active compounds selected from the group consisting of an HMG-CoA reductase inhibitor, an anti-obesity agent, and an antidiabetic agent, and (3) a pharmaceutically acceptable carrier.

30. A pharmaceutical composition comprising:
(1) a compound of claim 1,
(2) one or more pharmaceutically active compounds selected from the group consisting of:
(a) insulin sensitizers, PPAR-gamma agonists, partial agonists, and antagonists, PPAR-alpha agonists, PPAR-delta agonsts, and biguanides;
(b) insulin and insulin mimetics;
(c) sulfonylureas;
(d) α-glucosidase inhibitors;
(e) cholesterol lowering agents selected from the group consisting of (i) HMG-CoA reductase inhibitors; (ii) sequestrants, (iii) nicotinyl alcohol, nicotinic acid and salts thereof, (iv) PPARα agonists, (v) inhibitors of cholesterol absorption; and (vi) probucol;
(f) PPARα/γ agonists;
(g) antiobesity compounds selected from the group consisting of appetite suppressants, fenfluramine, dexfenfluramine, phentiramine, sulbitramine, orlistat, neuropeptide Y5 inhibitors (NP Y5 receptor antagonosts), leptin, β₃ adrenergic receptor agonists, and PPARγ antagonists and partial agonists;
(h) ileal bile acid transporter inhibitors; and
(i) insulin receptor activators; and
(3) a pharmaceutically acceptable carrier.

31. A compound in accordance with claim 1 having the structure

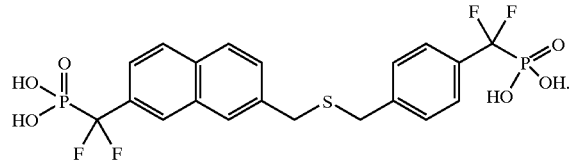

* * * * *